United States Patent [19]

Short

[11] Patent Number: 6,057,103

[45] Date of Patent: May 2, 2000

[54] SCREENING FOR NOVEL BIOACTIVITIES

[75] Inventor: Jay M. Short, Encinitas, Calif.

[73] Assignee: Diversa Corporation, San Diego, Calif.

[21] Appl. No.: 08/918,406

[22] Filed: Aug. 26, 1997

Related U.S. Application Data

[63] Continuation-in-part of application No. 08/657,409, Jun. 3, 1996, Pat. No. 5,958,672, which is a continuation-in-part of application No. 08/568,994, Dec. 7, 1995, abandoned, which is a continuation-in-part of application No. 08/503,606, Jul. 18, 1995, abandoned.

[51] Int. Cl.$^7$ .............................. C12Q 1/68; C12P 19/34; C07H 21/02; C07H 21/04

[52] U.S. Cl. ........................... 435/6; 435/91.1; 435/91.2; 435/172.3; 536/231; 536/24.3; 536/24.31; 536/24.32; 536/24.33; 536/25.4; 436/501

[58] Field of Search .............................. 435/6, 91.1, 91.2, 435/172.3; 536/23.1, 24.3, 24.31, 24.32, 24.33, 25.4; 436/501

[56] References Cited

U.S. PATENT DOCUMENTS

| | | | |
|---|---|---|---|
| 5,605,793 | 2/1997 | Stemmer | 435/6 |
| 5,783,431 | 7/1998 | Peterson et al. | 435/172.3 |
| 5,824,485 | 10/1998 | Thompson et al. | 435/6 |

FOREIGN PATENT DOCUMENTS

WO 96/34112  10/1996  WIPO .

OTHER PUBLICATIONS

Dynal Technical Handbook, "Biomagnetic Techniques in Molecular Biology", pp. 78–89, 1995.

Nakamura et al, "The murine lymphotoxin–B receptor cDNA: isolation by the signal sequences trap and chromosomal mapping", Genomics 30:312–319, 1995.

Eberwine et al, "Isolation of enzyme cDNA clones by enzyme immunodetection assay: Isolation of a peptide acetyltransferase", Proc. Natl. Acad. Sci. 84:1449–1453, Mar. 1987.

*Primary Examiner*—Jeffrey Fredman
*Attorney, Agent, or Firm*—Gray Cary Ware & Freidenrich LLP; Lisa A. Haile

[57] ABSTRACT

Disclosed is a process for identifying clones having a specified activity of interest, which process comprises (i) generating one or more expression libraries derived from nucleic acid directly isolated from the environment; and (ii) screening said libraries utilizing an assay system. More particularly, this is a process for identifying clones having a specified activity of interest by (i) generating one or more expression libraries derived from nucleic acid directly or indirectly isolated from the environment; (ii) exposing said libraries to a particular substrate or substrates of interest; and (iii) screening said exposed libraries utilizing a fluorescence activated cell sorter to identify clones which react with the substrate or substrates. Also provided is a process for identifying clones having a specified activity of interest by (i) generating one or more expression libraries derived from nucleic acid directly or indirectly isolated from the environment; and (ii) screening said exposed libraries utilizing an assay requiring a binding event or the covalent modification of a target, and a fluorescence activated cell sorter to identify positive clones.

33 Claims, 8 Drawing Sheets

*1. Concentrate bacteria, digest protein and preserve MW (> 100 kbp) DNA*

*2. Partially digest DNA. Separate by PFGE. Size select for cloning.*

*3. Ligate to fosmid arms λ package and transfect to E. coli. Array library in microtiter plates.*

1. Concentrate bacteria, digest protein and preserve MW (> 100 kbp) DNA
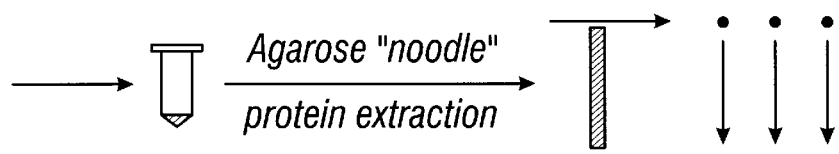
2. Partially digest DNA. Separate by PFGE. Size select for cloning.
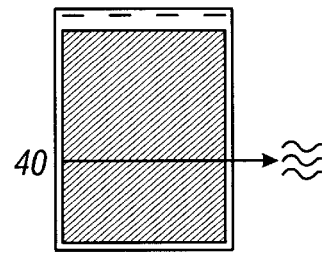
3. Ligate to fosmid arms λ package and transfect to E. coli. Array library in microtiter plates.
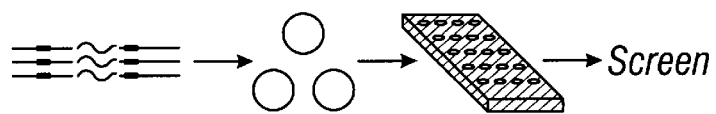
*FIG. 1*

```
Saccharopo 352(SEQ ID NO:3)
GCCGCCGACACCCCGATCACGCGCCGATCGTGGTGTCCTGCTTCGACGCCA
TCAAGGCGACC coelicolor 343(SEQ ID NO:4)
GCCGCCGACACCCCGATCACCCCGATCGTCGTCGCCTGCTTCGACGCGA
TCCGCGCCAC Gvenzuelae 337(SEQ ID NO:5)
TCCTCGGACGCCCCGATCTCCCCGATCACGATGGCCTGCTTCGACGCCA
TCAAGGCGACC fraidiane 352(SEQ ID NO:6)
GCGGCCGACGCCCCGATCTCGCCCATCACCGTGGCCTGCTTCGATGCGA
TCAAGGCGACC glaucescen 343(SEQ ID NO:7)
GCCACCGACGCGCCGATCTCCCCATCACCGTGGCCTGCTTCGACGCCA
TCAAGGCGAC Ggriseues 352(SEQ ID NO:8)
GCGGTGGACGCGCCGATCACCCGCTCACGATGGCGGCCTTCGACGCGA
TCCGCGCCACC E.coli 340(SEQ ID NO:9)
GGCGCAGAGAAAGCCAGTACGCCCGCGTTGGGCGTTGGTGGTTTTGGCGCG
GCACGTGCATTA
```

FIG. 2

SCREENING FOR NOVEL BIOACTIVITIES

This application is a continuation-in-part of U.S. application Ser. No. 08/657,409, which was filed on Jun. 3, 1996 now U.S. Pat. No. 5,958,672, which is a continuation-in-part of U.S. application Ser. No. 08/568,994 which was filed on Dec. 7, 1995 (now abandoned) which is a continuation-in-part of U.S. application Ser. No. 08/503,606 which was filed on Jul. 18, 1995 (now abandoned).

FIELD OF THE INVENTION

The present invention relates to the discovery of new bio-active molecules, such as antibiotics, anti-virals, anti-tumor agents and regulatory proteins. More particularly, the invention relates to a system for capturing genes potentially encoding novel biochemical pathways of interest in prokaryotic systems, and screening for these pathways utilizing high throughput screening assays.

BACKGROUND OF THE INVENTION

Within the last decade there has been a dramatic increase in the need for bioactive compounds with novel activities. This demand has arisen largely from changes in worldwide demographics coupled with the clear and increasing trend in the number of pathogenic organisms that are resistant to currently available antibiotics. For example, while there has been a surge in demand for antibacterial drugs in emerging nations with young populations, countries with aging populations, such as the US, require a growing repertoire of drugs against cancer, diabetes, arthritis and other debilitating conditions. The death rate from infectious diseases has increased 58% between 1980 and 1992 and it has been estimated that the emergence of antibiotic resistant microbes has added in excess of $30 billion annually to the cost of health care in the US alone. (Adams et al., *Chemical and Engineering News*, 1995; Amann et al., *Microbiological Reviews*, 59, 1995). As a response to this trend pharmaceutical companies have significantly increased their screening of microbial diversity for compounds with unique activities or specificities.

There are several common sources of lead compounds (drug candidates), including natural product collections, synthetic chemical collections, and synthetic combinatorial chemical libraries, such as nucleotides, peptides, or other polymeric molecules. Each of these sources has advantages and disadvantages. The success of programs to screen these candidates depends largely on the number of compounds entering the programs, and pharmaceutical companies have to date screened hundred of thousands of synthetic and natural compounds in search of lead compounds. Unfortunately, the ratio of novel to previously-discovered compounds has diminished with time. The discovery rate of novel lead compounds has not kept pace with demand despite the best efforts of pharmaceutical companies. There exists a strong need for accessing new sources of potential drug candidates.

The majority of bioactive compounds currently in use are derived from soil microorganisms. Many microbes inhabiting soils and other complex ecological communities produce a variety of compounds that increase their ability to survive and proliferate. These compounds are generally thought to be nonessential for growth of the organism and are synthesized with the aid of genes involved in intermediary metabolism hence their name—"secondary metabolites". Secondary metabolites that influence the growth or survival of other organisms are known as "bioactive" compounds and serve as key components of the chemical defense arsenal of both micro- and macroorganisms. Humans have exploited these compounds for use as antibiotics, antiinfectives and other bioactive compounds with activity against a broad range of prokaryotic and eukaryotic pathogens. Approximately 6,000 bioactive compounds of microbial origin have been characterized, with more than 60% produced by the gram positive soil bacteria of the genus Streptomyces. (Barnes et al., *Proc.Nat. Acad. Sci. U.S.A.*, 91, 1994). Of these, at least 70 are currently used for biomedical and agricultural applications. The largest class of bioactive compounds, the polyketides, include a broad range of antibiotics, immunosuppressants and anticancer agents which together account for sales of over $5 billion per year.

Despite the seemingly large number of available bioactive compounds, it is clear that one of the greatest challenges facing modern biomedical science is the proliferation of antibiotic resistant pathogens. Because of their short generation time and ability to readily exchange genetic information, pathogenic microbes have rapidly evolved and disseminated resistance mechanisms against virtually all classes of antibiotic compounds. For example, there are virulent strains of the human pathogens Staphylococcus and Streptococcus that can now be treated with but a single antibiotic, vancomycin, and resistance to this compound will require only the transfer of a single gene, vanA, from resistant Enterococcus species for this to occur. (Bateson et al., *System. Appl. Microbiol*, 12, 1989). When this crucial need for novel antibacterial compounds is superimposed on the growing demand for enzyme inhibitors, immunosuppressants and anti-cancer agents it becomes readily apparent why pharmaceutical companies have stepped up their screening of microbial diversity for bioactive compounds with novel properties.

The approach currently used to screen microbes for new bioactive compounds has been largely unchanged since the inception of the field. New isolates of bacteria, particularly gram positive strains from soil environments, are collected and their metabolites tested for pharmacological activity. A more recent approach has been to use recombinant techniques to synthesize hybrid antibiotic pathways by combining gene subunits from previously characterized pathways. This approach, called "combinatorial biosynthesis" has focused primarily on the polyketide antibiotics and has resulted in a number of structurally unique compounds which have displayed activity. (Betz et al., *Cytometry*, 5, 1984; Davey et al., *Microbiological Reviews*, 60, 1989). However, compounds with novel antibiotic activities have not yet been reported; an observation that may be do to the fact that the pathway subunits are derived from those encoding previously characterized compounds. Dramatic success in using recombinant approaches due to small molecule synthesis has been recently reported in the engineering of biosynthetic pathways to increase the production of desirable antibiotics. (Diaper et al., *Appl. Bacteriol.*, 77, 1994; Enzyme Nomenclature, Academic Press: NY, 1992).

There is still tremendous biodiversity that remains untapped as the source of lead compounds. However, the currently available methods for screening and producing lead compounds cannot be applied efficiently to these under-explored resources. For instance, it is estimated that at least 99% of marine bacteria species do not survive on laboratory media, and commercially available fermentation equipment is not optimal for use in the conditions under which these species will grow, hence these organisms are difficult or impossible to culture for screening or re-supply. Recollection, growth, strain improvement, media improvement and scale-up production of the drug-producing organisms often pose problems for synthesis and development of lead compounds. Furthermore, the need for the interaction of specific organisms to synthesize some compounds makes their use in discovery extremely difficult. New methods to harness the genetic resources and chemical diversity of these untapped sources of compounds for use in drug discovery are very valuable. The present invention provides a path to access this untapped biodiversity and to rapidly screen for activities of interest utilizing recombinant DNA technology. This invention combines the benefits associated with the ability to rapidly screen natural compounds with the flexibility and reproducibility afforded with working with the genetic material of organisms.

The present invention allows one to identify genes encoding bioactivities of interest from complex environmental gene expression libraries, and to manipulate cloned pathways to evolve recombinant small molecules with unique activities. Bacteria and many eukaryotes have a coordinated mechanism for regulating genes whose products are involved in related processes. The genes are clustered, in structures referred to as "gene clusters," on a single chromosome and are transcribed together under the control of a single regulatory sequence, including a single promoter which initiates transcription of the entire cluster. The gene cluster, the promoter, and additional sequences that function in regulation altogether are referred to as an "operon" and can include up to 20 or more genes, usually from 2 to 6 genes. Thus, a gene cluster is a group of adjacent genes that are either identical or related, usually as to their function. Gene clusters are of interest in drug discovery processes since product(s) of gene clusters include, for example, antibiotics, antivirals, antitumor agents and regulatory proteins.

Some gene families consist of one or more identical members. Clustering is a prerequisite for maintaining identity between genes, although clustered genes are not necessarily identical. Gene clusters range from extremes where a duplication is generated of adjacent related genes to cases where hundreds of identical genes lie in a tandem array. Sometimes no significance is discernable in a repetition of a particular gene. A principal example of this is the expressed duplicate insulin genes in some species, whereas a single insulin gene is adequate in other mammalian species.

Gene clusters undergo continual reorganization and, thus, the ability to create heterogeneous libraries of gene clusters from, for example, bacterial or other prokaryote sources is valuable in determining sources of novel bioactivities, including enzymes such as, for example, the polyketide synthases that are responsible for the synthesis of polyketides having a vast array of useful activities.

Polyketides are molecules which are an extremely rich source of bioactivities, including antibiotics (such as tetracyclines and erythromycin), anti-cancer agents (daunomycin), immunosuppressants (FK506 and rapamycin), and veterinary products (monensin). Many polyketides (produced by polyketide synthases) are valuable as therapeutic agents. Polyketide synthases (PKSs) are multifunctional enzymes that catalyze the biosynthesis of a huge variety of carbon chains differing in length and patterns of functionality and cyclization. Despite their apparent structural diversity, they are synthesized by a common pathway in which units derived from acetate or propionate are condensed onto the growing chain in a process resembling fatty acid biosynthesis. The intermediates remain bound to the polyketide synthase during multiple cycles of chain extension and (to a variable extent) reduction of the ($\beta$-ketone group formed in each condensation. The structural variation between naturally occurring polyketides arises largely from the way in which each PKS controls the number and type of units added, and from the extent and stereochemistry of reduction at each cycle. Still greater diversity is produced by the action of regiospecific glycosylases, methyltransferases and oxidative enzymes on the product of the PKS.

Polyketide synthase genes fall into gene clusters. At least one type (designated type I) of polyketide synthases have large size genes and encoded enzymes, complicating genetic manipulation and in vitro studies of these genes/proteins. Progress in understanding the enzymology of such type I systems have previously been frustrated by the lack of cell-free systems to study polyketide chain synthesis by any of these multienzymes, although several partial reactions of certain pathways have been successfully assayed in vitro. Cell-free enzymatic synthesis of complex polyketides has proved unsuccessful, despite more than 30 years of intense efforts, presumably because of the difficulties in isolating fully active forms of these large, poorly expressed multifunctional proteins from naturally occurring producer organisms, and because of the relative lability of intermediates formed during the course of polyketide biosynthesis. In an attempt to overcome some of these limitations, modular PKS subunits have been expressed in heterologous hosts such as *Escherichia coli* and *Streptomyces coelicolor*. Whereas the proteins expressed in *E. coli* are not fully active, heterologous expression of certain PKSs in *S. coelicolor* resulted in the production of active protein. Cell-free enzymatic synthesis of polyketides from PKSs with substantially fewer active sites, such as the 6-methylsalicylate synthase, chalcone synthase, tetracenomycin synthase, and the PKS responsible for the polyketide component of cyclosporin, have been reported.

Hence, studies have indicated that in vitro synthesis of polyketides is possible, however, synthesis was always performed with purified enzymes. Heterologous expression of genes encoding PKS modular subunits have allowed synthesis of functional polyketides in vivo, however, there are several challenges presented by this approach, which had to be overcome. The large sizes of modular PKS gene clusters (>30 kb) make their manipulation on plasmids difficult. Modular PKSs also often utilize substrates which may be absent in a heterologous host. Finally, proper folding, assembly, and posttranslational modification of very large foreign polypeptides are not guaranteed.

Novel systems to clone and screen for bioactivities of interest in vitro are desirable. The method(s) of the present invention allow the cloning and discovery of novel bioactive molecules in vitro, and in particular novel bioactive molecules derived from uncultivated samples. Large size gene clusters can be cloned and screened using the method(s) of the present invention. Unlike previous strategies, the method (s) of the present invention allow one to clone utilizing well known genetic systems, and to screen in vitro with crude (impure) preparations.

SUMMARY OF THE INVENTION

The present invention allows one to clone genes potentially encoding novel biochemical pathways of interest in prokaryotic systems, and screen for these pathways utilizing a novel process. Sources of the genes may be isolated, individual organisms ("isolates"), collections of organisms that have been grown in defined media ("enrichment cultures"), or, most preferably, uncultivated organisms ("environmental samples"). The use of a culture-independent approach to directly clone genes encoding novel bioactivities from environmental samples is most preferable since it allows one to access untapped resources of biodiversity.

"Environmental libraries" are generated from environmental samples and represent the collective genomes of naturally occurring organisms archived in cloning vectors that can be propagated in suitable prokaryotic hosts. Because the cloned DNA is initially extracted directly from environmental samples, the libraries are not limited to the small fraction of prokaryotes that can be grown in pure culture. Additionally, a normalization of the environmental DNA present in these samples could allow more equal representation of the DNA from all of the species present in the original sample. This can dramatically increase the efficiency of finding interesting genes from minor constituents of the sample which may be under-represented by several orders of magnitude compared to the dominant species.

In the evaluation of complex environmental expression libraries, a rate limiting step occurs at the level of discovery of bioactivities. The present invention allows the rapid screening of complex environmental expression libraries, containing, for example, thousands of different organisms.

In the present invention, for example, gene libraries generated from one or more uncultivated microorganisms are screened for an activity of interest. Potential pathways encoding bioactive molecules of interest are first captured in prokaryotic cells in the form of gene expression libraries; crude or partially purified extracts, or pure proteins from metabolically rich cell lines are then combined with the gene expression libraries to create potentially active molecules; and the combination is screened for an activity of interest.

Common approaches to drug discovery involve screening assays in which disease targets (macromolecules implicated in causing a disease) are exposed to potential drug candidates which are tested for therapeutic activity. In other approaches, whole cells or organisms that are representative of the causative agent of the disease, such as bacteria or tumor cell lines, are exposed to the potential candidates for screening purposes. Any of these approaches can be employed with the present invention.

The present invention also allows for the transfer of cloned pathways derived from uncultivated samples into metabolically rich hosts for heterologous expression and downstream screening for bioactive compounds of interest using a variety of screening approaches briefly described above.

Accordingly, in one aspect, the present invention provides a process for identifying clones encoding a specified activity of interest, which process comprises (i) generating one or more expression libraries derived from nucleic acid directly isolated from the environment; and (ii) combining the expression libraries with crude or partially purified extracts, or pure proteins from metabolically rich cell lines; and (iii) screening said libraries utilizing any of a variety of screening assays to identify said clones.

In another aspect, the present invention provides a process for identifying clones encoding a specified activity of interest, which process comprises (i) generating one or more expression libraries derived from nucleic acid directly isolated from the environment; and (ii) transferring the clones into a metabolically rich cell line; and (iii) screening said cell line utilizing any of a variety of screening assays to identify said clones.

BRIEF DESCRIPTION OF THE DRAWINGS

FIG. 1 shows a scheme to capture, clone and archive large genome fragments from uncultivated microbes from natural environments. The cloning vectors used in this process can archive from 40 kbp (fosmids) to greater than 100 kbp (BACs).

FIG. 2 shows the nucleotide alignment of a region of the ketosynthase I gene of polyketide pathways from a variety of Streptomyces species. These regions are aligned with a homologous region encoding a fatty acid synthase from E. coli. Observed sequence differences were used to construct probes that hybridize to cloned polyketide sequences but not to fatty acid sequences carried by the E. Coli host strain.

DETAILED DESCRIPTION OF PREFERRED EMBODIMENTS

Sample Source/Collection

Figure 3:
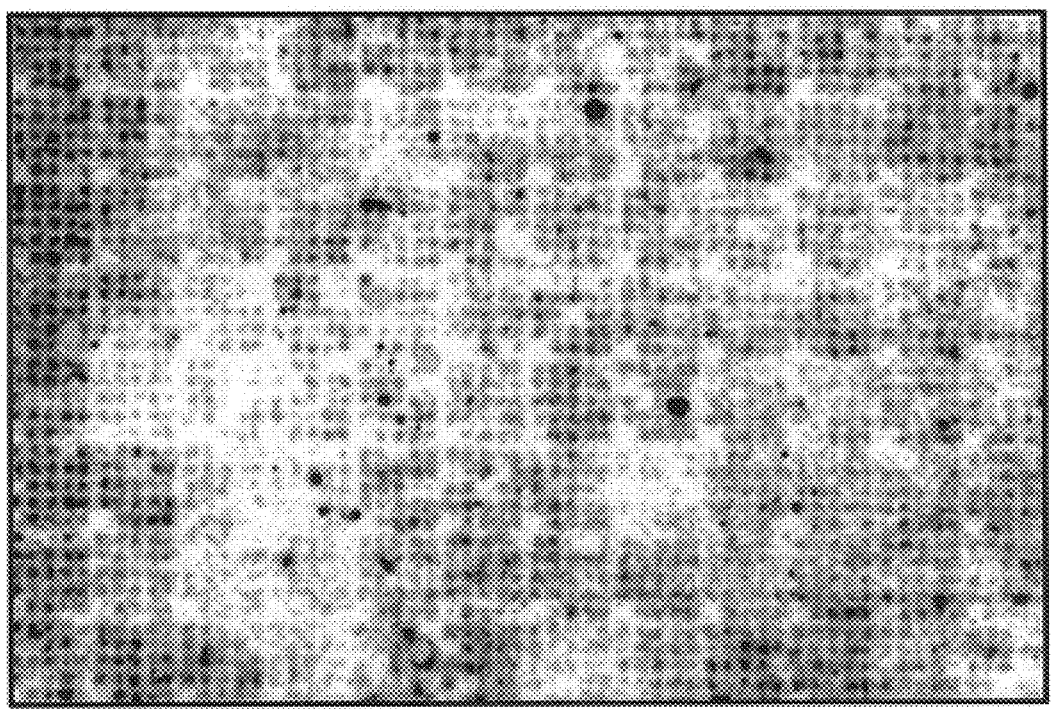
FIG. 3 shows an example of a high density filter array of environmental fosmid clones probed with a labeled oligonucleotide probe. The 2400 arrayed clones contain approximately 96 million base pairs of DNA cloned from a naturally occurring microbial community.
Figures 4A, 4B:
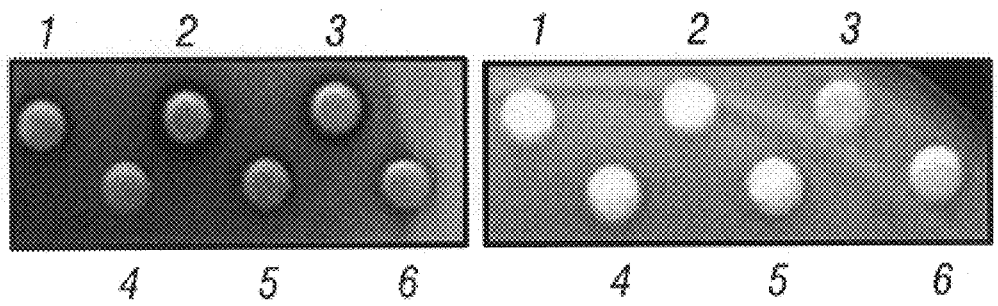
FIG. 4 shows the results of mixed extract experiment measuring conferral of bioactivity on recombinant backbones heterologously expressed in E. coli. A. Organic extracts from 3 oxytetracylin clones (1–3) and 3 gramicidin clones (4–6) were incubated with a protein extract from Streptomyces lividans strain TK24. After incubation the mixture was reextracted with methyl ethyl ketone, spotted on to filter disks, allowed to dry, then placed on a lawn of an E. coli test strain. Distinct zones of clearing can be seen around disks 2, 3 and 5. Extracts from 2 and 3 were subsequently seperated by thin layer chromatography which showed UV fluorescent spots with similar Rf and appearance to authentic oxytetracylin. B. Filters corresponding to those in A but without incubation with protein extract from Streptomyces. The Streptomyces extract alone also showed no bioactivity.

The method of the present invention begins with the construction of gene libraries which represent the collective genomes of naturally occurring organisms archived in cloning vectors that can be propagated in suitable prokaryotic hosts.

The microorganisms from which the libraries may be prepared include prokaryotic microorganisms, such as Eubacteria and Archaebacteria, and lower eukaryotic microorganisms such as fungi, some algae and protozoa. Libraries may be produced from environmental samples in which case DNA may be recovered without culturing of an organism or the DNA may be recovered from one or more cultured organisms. Such microorganisms may be extremophiles, such as hyperthermophiles, psychrophiles, psychrotrophs, halophiles, barophiles, acidophiles, etc.

The microorganisms from which the libraries may be prepared may be collected using a variety of techniques known in the art. Samples may also be collected using the methods detailed in the example provided below. Briefly, the example below provides a method of selective in situ enrichment of bacterial and archaeal species while at the same time inhibiting the proliferation of eukaryotic members of the population. In situ enrichments can to increase the likelihood of recovering rare species and previously uncultivated members of a microbial population. If one desires to obtain bacterial and archaeal species, nucleic acids from eukaryotes in an environmental sample can seriously complicate DNA library construction and decrease the number of desired bacterial species by grazing. The method described below employs selective agents, such as antifungal agents, to inhibit the growth of eukaryotic species.

In situ enrichment is achieved by using a microbial containment device composed of growth substrates and nutritional amendments with the intent to lure, selectively, members of the surrounding environmental matrix. Choice of substrates (carbon sources) and nutritional amendments (ie, nitrogen, phosphorous, etc.) is dependent upon the members of the community for which one desires to enrich. Selective agents against eukaryotic members are also added to the trap. Again, the exact composition depends upon which members of the community one desires to enrich and which members of the community one desires to inhibit. Some of the enrichment "media" which may be useful in pulling out particular members of the community is described in the example provided herein.

Sources of microorganism DNA as a starting material library from which target DNA is obtained are particularly contemplated to include environmental samples, such as microbial samples obtained from Arctic and Antarctic ice, water or permafrost sources, materials of volcanic origin, materials from soil or plant sources in tropical areas, etc. Thus, for example, genomic DNA may be recovered from either a culturable or non-culturable organism and employed to produce an appropriate recombinant expression library for subsequent determination of a biological activity.

DNA Isolation

The preparation of DNA from the sample is an important step in the generation DNA libraries from environmental samples composed of uncultivated organisms, or for the generation of libraries from cultivated organisms. DNA can be isolated from samples using various techniques well known in the art (Nucleic Acids in the Environment Methods & Applications, J. T. Trevors, D. D. van Elsas, Springer Laboratory, 1995). Preferably, DNA obtained will be of large size and free of enzyme inhibitors or other contaminants. DNA can be isolated directly from an environmental sample (direct lysis), or cells may be harvested from the sample prior to DNA recovery (cell separation). Direct lysis procedures have several advantages over protocols based on cell separation. The direct lysis technique provides more DNA with a generally higher representation of the microbial community, however, it is sometimes smaller in size and more likely to contain enzyme inhibitors than DNA recovered using the cell separation technique. Very useful direct lysis techniques have been described which provide DNA of high molecular weight and high purity (Barns, 1994; Holben, 1994). If inhibitors are present, there are several protocols which utilize cell isolation which can be employed (Holben, 1994). Additionally, a fractionation technique, such as the bis-benzimide separation (cesium chloride isolation) described herein, can be used to enhance the purity of the DNA.

Isolation of total genomic DNA from extreme environmental samples varies depending on the source and quantity of material. Uncontaminated, good quality (>20 kbp) DNA is required for the construction of a representative library for the present invention. A successful general DNA isolation protocol is the standard cetyl-trimethyl-ammonium-bromide (CTAB) precipitation technique. A biomass pellet is lysed and proteins digested by the nonspecific protease, proteinase K, in the presence of the detergent SDS. At elevated temperatures and high salt concentrations, CTAB forms insoluble complexes with denatured protein, polysaccharides and cell debris. Chloroform extractions are performed until the white interface containing the CTAB complexes is reduced substantially. The nucleic acids in the supernatant are precipitated with isopropanol and resuspended in TE buffer.

For cells which are recalcitrant to lysis, a combination of chemical and mechanical methods with cocktails of various cell-lysing enzymes may be employed. Isolated nucleic acid may then further be purified using small cesium gradients.

A further example of an isolation strategy is detailed in an example below. This type of isolation strategy is optimal for obtaining good quality, large size DNA fragments for cloning.

Normalization

The present invention can further optimize methods for isolation of activities of interest from a variety of sources, including consortias of microorganisms, primary enrichments, and environmental "uncultivated" samples. Libraries which have been "normalized" in their representation of the genome populations in the original samples are possible with the present invention. These libraries can then be screened utilizing the methods of the present invention, for enzyme and other bioactivities of interest.

Libraries with equivalent representation of genomes from microbes that can differ vastly in abundance in natural populations are generated and screened. This "normalization" approach reduces the redundancy of clones from abundant species and increases the representation of clones from rare species. These normalized libraries allow for greater screening efficiency resulting in the identification of cells encoding novel biological catalysts.

In one embodiment, viable or non-viable cells isolated from the environment are, prior to the isolation of nucleic acid for generation of the expression gene library, FACS sorted to separate cells from the sample based on, for instance, DNA or AT/GC content of the cells. Various dyes or stains well known in the art, for example those described in "Practical Flow Cytometry", 1995 Wiley-Liss, Inc., Howard M. Shapiro, M.D., are used to intercalate or associate with nucleic acid of cells, and cells are separated on the FACS based on relative DNA content or AT/GC DNA content in the cells. Other criteria can be used to separate cells from the sample, as well. DNA is then isolated from the cells and used for the generation of expression gene libraries, which are then screened for activities of interest.

Alternatively, the nucleic acid is isolated directly from the environment and is, prior to generation of the gene library, sorted based on DNA or AT/GC content. DNA isolated directly from the environment, is used intact, randomly sheared or digested to general fragmented DNA. The DNA is then bound to an intercalating agent as described above, and separated on the analyzer based on relative base content to isolate DNA of interest. Sorted DNA is then used for the generation of gene libraries, which are then screened for activities of interest.

As indicated, one embodiment for forming a normalized library from an environmental sample begins with the isolation of nucleic acid from the sample. This nucleic acid can then be fractionated prior to normalization to increase the chances of cloning DNA from minor species from the pool of organisms sampled. DNA can be fractionated using a density centrifugation technique, such as a cesium-chloride gradient. When an intercalating agent, such as bis-benzimide is employed to change the buoyant density of the nucleic acid, gradients will fractionate the DNA based on relative base content. Nucleic acid from multiple organisms can be separated in this manner, and this technique can be used to fractionate complex mixtures of genomes. This can be of particular value when working with complex environmental samples. Alternatively, the DNA does not have to be fractionated prior to normalization. Samples are recovered from the fractionated DNA, and the strands of nucleic acid are then melted and allowed to selectively reanneal under fixed conditions(Cot driven hybridization). When a mixture of nucleic acid fragments is melted and allowed to reanneal under stringent conditions, the common sequences find their complementary strands faster than the rare sequences. After an optional single-stranded nucleic acid isolation step, single-stranded nucleic acid representing an enrichment of rare sequences is amplified using techniques well known in the art, such as a polymerase chain reaction (Barnes, 1994), and used to generate gene libraries. This procedure leads to the amplification of rare or low abundance nucleic acid molecules, which are then used to generate a gene library which can be screened for a desired bioactivity. While DNA will be recovered, the identification of the organism(s) originally containing the DNA may be lost. This method offers the ability to recover DNA from "unclonable" sources. This method is further detailed in the example below.

Hence, one embodiment for forming a normalized library from environmental sample(s) is by (a) isolating nucleic acid from the environmental sample(s); (b) optionally fractionating the nucleic acid and recovering desired fractions; (c) normalizing the representation of the DNA within the population so as to form a normalized expression library from the DNA of the environmental sample(s). The normalization process is described and exemplified in detail in co-pending, commonly assigned U.S. Ser. No. 08/665,565, filed Jun. 18, 1996.

Gene Libraries

Gene libraries can be generated by inserting the normalized or non-normalized DNA isolated or derived from a sample into a vector or a plasmid. Such vectors or plasmids are preferably those containing expression regulatory sequences, including promoters, enhancers and the like. Such polynucleotides can be part of a vector and/or a composition and still be isolated, in that such vector or composition is not part of its natural environment. Particularly preferred phage or plasmids and methods for introduction and packaging into them are described herein.

The examples below detail procedures for producing libraries from both cultured and non-cultured organisms.

Cloning of DNA fragments prepared by random cleavage of the target DNA can also be used to generate a representative library. DNA dissolved in TE buffer is vigorously passed through a 25 gauge double-hubbed needle until the sheared fragments are in the desired size range. The DNA ends are "polished" or blunted with Mung Bean Nuclease, and EcoRI restriction sites in the target DNA are protected with EcoRI Methylase. EcoRI linkers (GGAATTCC) are ligated to the blunted/protected DNA using a very high molar ratio of linkers to target DNA. This lowers the probability of two DNA molecules ligating together to create a chimeric clone. The linkers are cut back with EcoRI restriction endonuclease and the DNA is size fractionated. The removal of sub-optimal DNA fragments and the small linkers is critical because ligation to the vector will result in recombinant molecules that are unpackageable, or the construction of a library containing only linkers as inserts. Sucrose gradient fractionation is used since it is extremely easy, rapid and reliable. Although the sucrose gradients do not provide the resolution of agarose gel isolations, they do produce DNA that is relatively free of inhibiting contaminants. The prepared target DNA is ligated to the lambda vector, packaged using in vitro packaging extracts and grown on the appropriate *E. coli*.

As representative examples of expression vectors which may be used there may be mentioned viral particles, baculovirus, phage, plasmids, phagemids, cosmids, fosmids, bacterial artificial chromosomes, viral DNA (e.g. vaccinia, adenovirus, foul pox virus, pseudorabies and derivatives of SV40), P1-based artificial chromosomes, yeast plasmids, yeast artificial chromosomes, and any other vectors specific for specific hosts of interest (such as bacillus, aspergillus, yeast, etc.) Thus, for example, the DNA may be included in any one of a variety of expression vectors for expressing a polypeptide. Such vectors include chromosomal, nonchromosomal and synthetic DNA sequences. Large numbers of suitable vectors are known to those of skill in the art, and are commercially available. The following vectors are provided by way of example; Bacterial: pQE vectors (Qiagen), pBluescript plasmids, pNH vectors, (lambda-ZAP vectors (Stratagene); ptrc99a, pKK223-3, pDR540, pRIT2T (Pharmacia); Eukaryotic: pXT1, pSG5 (Stratagene), pSVK3, pBPV, pMSG, pSVLSV40 (Pharmacia). However, any other plasmid or other vector may be used as long as they are replicable and viable in the host. Low copy number or high copy number vectors may be employed with the present invention.

A preferred type of vector for use in the present invention contains an f-factor origin replication. The f-factor (or fertility factor) in *E. coli* is a plasmid which effects high frequency transfer of itself during conjugation and less frequent transfer of the bacterial chromosome itself A particularly preferred embodiment is to use cloning vectors, referred to as "fosmids" or bacterial artificial chromosome (BAC) vectors. These are derived from *E. coli* f-factor which is able to stably integrate large segments of genomic DNA. When integrated with DNA from a mixed uncultured environmental sample, this makes it possible to achieve large genomic fragments in the form of a stable "environmental DNA library."

Another preferred type of vector for use in the present invention is a cosmid vector. Cosmid vectors were originally designed to clone and propagate large segments of genomic DNA. Cloning into cosmid vectors is described in detail in Sambrook, et al., Molecular Cloning A Laboratory Manual, Second Edition, Cold Spring Harbor Laboratory Press, 1989.

The DNA sequence in the expression vector is operatively linked to an appropriate expression control sequence(s)

(promoter) to direct RNA synthesis. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art. The expression vector also contains a ribosome binding site for translation initiation and a transcription terminator. The vector may also include appropriate sequences for amplifying expression. Promoter regions can be selected from any desired gene using CAT (chloramphenicol transferase) vectors or other vectors with selectable markers.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium.

The cloning strategy permits expression via both vector driven and endogenous promoters; vector promotion may be important with expression of genes whose endogenous promoter will not function in *E. coli*.

The DNA derived from a microorganism(s) may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA selected and isolated as hereinabove described is introduced into a suitable host to prepare a library which is screened for the desired activity. The selected DNA is preferably already in a vector which includes appropriate control sequences whereby selected DNA which encodes for a bio-activity may be expressed, for detection of the desired activity. The host cell is a prokaryotic cell, such as a bacterial cell. Particularly preferred host cells are *E. coli*. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)). The selection of an appropriate host is deemed to be within the scope of those skilled in the art from the teachings herein.

Host cells are genetically engineered (transduced or transformed or transfected) with the vectors. The engineered host cells can be cultured in conventional nutrient media modified as appropriate for activating promoters, selecting transformants or amplifying genes. The culture conditions, such as temperature, pH and the like, are those previously used with the host cell selected for expression, and will be apparent to the ordinarily skilled artisan.

Since it appears that many bioactive compounds of bacterial origin are encoded in contiguous multigene pathways varying from 15 to 100 kbp, cloning large genome fragments is preferred with the present invention, in order to express novel pathways from natural assemblages of microorganisms. Capturing and replicating DNA fragments of 40 to 100 kbp in surrogate hosts such as *E. coli*, Bacillus or Streptomyces is in effect "propagating" uncultivated microbes, albeit in the form of large DNA fragments each representing from 2 to 5% of a typical eubacterial genome.

Two hurdles that must be overcome to successfully capture large genome fragments from naturally occurring microbes and to express multigene pathways from subsequent clones are 1) the low cloning efficiency of environmental DNA and 2) the inherent instability of large clones. To overcome these hurdles, high quality large molecular weight DNA is extracted directly from soil and other environments and vectors such as the F factor based Bacterial Artificial Chromosome (BAC) vectors are used to efficiently clone and propagate large genome fragments. The environmental library approach (FIG. 1) will process such samples with an aim to archive and replicate with a high degree of fidelity the collective genomes in the mixed microbial assemblage. The basis of this approach is the application of modified Bacterial Artificial Chromosome (BAC) vectors to stably propagate 100–200 kbp genome fragments. The BAC vector and its derivative the fosmid (for F factor based cosmid) use the f-origin of replication to maintain copy number at one or two per cell. This feature has been shown to be a crucial factor in maintaining stability of large cloned fragments. High fidelity replication is especially important in propagating libraries comprised of high GC organisms such as the Streptomyces from which clones may be prone to rearrangement and deletion of duplicate sequences.

Because the fosmid vector uses the highly efficient lambda packaging system, comprehensive libraries can be assembled with a minimal amount of starting DNA. Environmental fosmid libraries of $4 \times 10^7$ clones of the present invention can be generated, each containing approximately 40 kbp of cloned DNA, from 100 ng of purified DNA collected from samples, including, for example, from the microbial containment device described herein.

A potential problem with constructing libraries for the expression of bioactive compounds in *E. coli* is that this gram-negative bacterium may not have the appropriate genetic background to express the compounds in their active form. One aspect of the present invention allows the efficient cloning of fragments in *E. coli* and the subsequent transfer to a different suitable host for expression and screening. Shuttle vectors, which allow propagation in two different types of hosts, can be utilized in the present invention to clone and propagate in bacterial hosts, such as *E. coli*, and transfer to alternative hosts for expression of active molecules. Such alternative hosts may include but are not limited to, for example, Streptomyces or Bacillus, or other metabolically rich hosts such as Cyanobacteria, Myxobacteria, etc. *Streptomyces lividans*, for example, may be used as the expression host for the cloned pathways. This strain is routinely used in the recombinant expression of heterologous antibiotic pathways because it recognized a large number of promoters and appears to lack a restriction system (Guseck, T. W. & Kinsella, J. E., (1992) *Crit. Rev. Microbiol.* 18, 247–260).

In the present invention, the example below describes a shuttle vector which can be utilized. The vector is an *E. coli*-Streptomyces shuttle vector. This system allows one to stably clone and express large inserts (40 kbp genome fragments). Chromosomally integrated recombinants can be recovered as the original fosmid to facilitate sequence characterization and further manipulation of positive clones. Replicons which allow regulation of the clone copy number in hosts can be utilized. For instance, the SPC2 replicon, a 32 kb fertility plasmid that is present at one copy per cell in *Streptomyces coelicolor*, can be utilized. This replicon can be "tuned" by truncation to replicate at various copy number in Streptomyces hosts. For instance, replicative versions of integrative shuttle vectors may be designed containing the full length and truncated SCP2 replicon which will regulate the clone copy number in the Streptomyces host from 1 to 10 copies per cell.

In order to ensure that the bioactivity of the clones containing the putative polyketide or other clustered genes is not due to the activation of any resident gene cluster, the resident gene sequences can be removed from the host strain by gene replacement or deletion. An example is presented below.

Biopanning

After the expression libraries have been generated one can include the additional step of "biopanning" such libraries prior to transfer to a second host for expression screening. The "biopanning" procedure refers to a process for identifying clones having a specified biological activity by screening for sequence homology in a library of clones prepared by (i) selectively isolating target DNA, from DNA derived from at least one microorganism, by use of at least one probe DNA comprising at least a portion of a DNA sequence encoding an biological having the specified biological activity; and (ii) transforming a host with isolated target DNA to produce a library of clones which are then processed for screening for the specified biological activity.

The probe DNA used for selectively isolating the target DNA of interest from the DNA derived from at least one microorganism can be a full-length coding region sequence or a partial coding region sequence of DNA for an known bioactivity. The original DNA library can be preferably probed using mixtures of probes comprising at least a portion of the DNA sequence encoding a known bioactivity having a desired activity. These probes or probe libraries are preferably single-stranded and the microbial DNA which is probed has preferably been converted into single-stranded form. The probes that are particularly suitable are those derived from DNA encoding bioactivities having an activity similar or identical to the specified bioactivity which is to be screened.

The probe DNA should be at least about 10 bases and preferably at least 15 bases. In one embodiment, an entire coding region of one part of a pathway may be employed as a probe. Conditions for the hybridization in which target DNA is selectively isolated by the use of at least one DNA probe will be designed to provide a hybridization stringency of at least about 50% sequence identity, more particularly a stringency providing for a sequence identity of at least about 70%.

Hybridization techniques for probing a microbial DNA library to isolate target DNA of potential interest are well known in the art and any of those which are described in the literature are suitable for use herein, particularly those which use a solid phase-bound, directly or indirectly bound, probe DNA for ease in separation from the remainder of the DNA derived from the microorganisms.

Preferably the probe DNA is "labeled" with one partner of a specific binding pair (i.e. a ligand) and the other partner of the pair is bound to a solid matrix to provide ease of separation of target from its source. The ligand and specific binding partner can be selected from, in either orientation, the following: (1) an antigen or hapten and an antibody or specific binding fragment thereof; (2) biotin or iminobiotin and avidin or streptavidin; (3) a sugar and a lectin specific therefor; (4) an enzyme and an inhibitor therefor; (5) an apoenzyme and cofactor; (6) complementary homopolymeric oligonucleotides; and (7) a hormone and a receptor therefor. The solid phase is preferably selected from: (1) a glass or polymeric surface; (2) a packed column of polymeric beads; and (3) magnetic or paramagnetic particles.

Further, it is optional but desirable to perform an amplification of the target DNA that has been isolated. In this embodiment the target DNA is separated from the probe DNA after isolation. It is then amplified before being used to transform hosts. Long PCR (Barnes, W M, Proc. Natl. Acad. Sci, USA, Mar. 15, 1994 ) can be used to amplify large DNA fragments (e.g., 35 kb). The double stranded DNA selected to include as at least a portion thereof a predetermined DNA sequence can be rendered single stranded, subjected to amplification and reannealed to provide amplified numbers of selected double stranded DNA. Numerous amplification methodologies are now well known in the art.

The selected DNA is then used for preparing a library for further processing and screening by transforming a suitable organism. Hosts, particularly those specifically identified herein as preferred, are transformed by artificial introduction of the vectors containing the target DNA by inoculation under conditions conducive for such transformation.

The resultant libraries of transformed clones are then processed for screening for clones which display an activity of interest. Clones can be shuttled in alternative hosts for expression of active compounds, or screened using methods described herein.

Having prepared a multiplicity of clones from DNA selectively isolated from an organism, such clones are screened for a specific activity and to identify the clones having the specified characteristics.

The screening for activity may be effected on individual expression clones or may be initially effected on a mixture of expression clones to ascertain whether or not the mixture has one or more specified activities. If the mixture has a specified activity, then the individual clones may be rescreened for such activity or for a more specific activity. Alternatively, encapsulation techniques such as gel microdroplets, may be employed to localize multiple clones in one location to be screened on a FACS machine for positive expressing clones within the group of clones which can then be broken out into individual clones to be screened again on a FACS machine to identify positive individual clones. Screening in this manner using a FACS machine is fully described in patent application Ser. No. 08/876,276 filed Jun. 16, 1997. Thus, for example, if a clone mixture has a desirable activity, then the individual clones may be recovered and rescreened utilizing a FACS machine to determine which of such clones has the specified desirable activity.

As described with respect to one of the above aspects, the invention provides a process for activity screening of clones containing selected DNA derived from a microorganism which process comprises:

screening a library for specified bioactivity, said library including a plurality of clones, said clones having been prepared by recovering from genomic DNA of a microorganism selected DNA, which DNA is selected by hybridization to at least one DNA sequence which is all or a portion of a DNA sequence encoding a bioactivity having a desirable activity; and transforming a host with the selected DNA to produce clones which are further processed and/or screened for the specified bioactivity.

In one embodiment, a DNA library derived from a microorganism is subjected to a selection procedure to select therefrom DNA which hybridizes to one or more probe DNA sequences which is all or a portion of a DNA sequence encoding an activity having a desirable activity by:

(a) rendering the double-stranded genomic DNA population into a single-stranded DNA population;

(b) contacting the single-stranded DNA population of (a) with the DNA probe bound to a ligand under conditions permissive of hybridization so as to produce a double-stranded complex of probe and members of the genomic DNA population which hybridize thereto;

(c) contacting the double-stranded complex of (b) with a solid phase specific binding partner for said ligand so as to produce a solid phase complex;

(d) separating the solid phase complex from the single-stranded DNA population of (b);

(e) releasing from the probe the members of the genomic population which had bound to the solid phase bound probe;

(f) forming double-stranded DNA from the members of the genomic population of (e);

(g) introducing the double-stranded DNA of (f) into a suitable host to form a library containing a plurality of clones containing the selected DNA; and (h) screening the library for the desired activity.

In another aspect, the process includes a preselection to recover DNA including signal or secretion sequences. In this manner it is possible to select from the genomic DNA population by hybridization as hereinabove described only DNA which includes a signal or secretion sequence. The following paragraphs describe the protocol for this embodiment of the invention, the nature and function of secretion signal sequences in general and a specific exemplary application of such sequences to an assay or selection process.

A particularly preferred embodiment of this aspect further comprises, after (a) but before (b) above, the steps of:

(a i) contacting the single-stranded DNA population of (a) with a ligand-bound oligonucleotide probe that is complementary to a secretion signal sequence unique to a given class of proteins under conditions permissive of hybridization to form a double-stranded complex;

(a ii) contacting the double-stranded complex of (a i) with a solid phase specific binding partner for said ligand so as to produce a solid phase complex;

(a iii) separating the solid phase complex from the single-stranded DNA population of (a);

(a iv) releasing the members of the genomic population which had bound to said solid phase bound probe; and (a v) separating the solid phase bound probe from the members of the genomic population which had bound thereto.

The DNA which has been selected and isolated to include a signal sequence is then subjected to the selection procedure hereinabove described to select and isolate therefrom DNA which binds to one or more probe DNA sequences derived from DNA encoding a bioactivity having a desirable bioactivity.

This procedure of "biopanning" is described and exemplified in U.S. Ser. No. 08/692,002, filed Aug. 2, 1996.

Further, it is possible to combine all the above embodiments such that a normalization step is performed prior to generation of the expression library, the expression library is then generated, the expression library so generated is then biopanned, and the biopanned expression library is then screened using a high throughput cell sorting and screening instrument. Thus there are a variety of options: i.e. (i) one can just generate the library and then screen it; (ii) normalize the target DNA, generate the expression library and screen it; (iii) normalize, generate the library, biopan and screen; or (iv) generate, biopan and screen the library.

The clones which are identified as having the specified activity may then be sequenced to identify the DNA sequence encoding a bioactivity having the specified activity. Thus, in accordance with the present invention it is possible to isolate and identify: (i) DNA encoding a bioactivity having a specified activity, (ii) bioactivities having such activity (including the amino acid sequence thereof) and (iii) produce recombinant molecules having such activity.

Screening

The present invention offers the ability to screen for many types of bioactivities. For instance, the ability to select and combine desired components from a library of polyketides and postpolyketide biosynthesis genes for generation of novel polyketides for study is appealing. The method(s) of the present invention make it possible to and facilitate the cloning of novel polyketide synthases, and other relevant pathways or genes encoding commercially relevant secondary metabolites, since one can generate gene banks with clones containing large inserts (especially when using vectors which can accept large inserts, such as the f-factor based vectors), which facilitates cloning of gene clusters.

Preferably, the gene cluster or pathway DNA is ligated into a vector, particularly wherein a vector further comprises expression regulatory sequences which can control and regulate the production of a detectable protein or protein-related array activity from the ligated gene clusters. Use of vectors which have an exceptionally large capacity for exogenous DNA introduction are particularly appropriate for use with such gene clusters and are described by way of example herein to include the f-factor (or fertility factor) of *E. coli*. As previously indicated, this f-factor of *E. coli* is a plasmid which affect high-frequency transfer of itself during conjugation and is ideal to achieve and stably propagate large DNA fragments, such as gene clusters from mixed microbial samples. Other examples of vectors include cosmids, bacterial artificial chromosome vectors (BAC vectors), and P1 vectors.

Gene expression libraries of the present invention, capturing potential pathways encoding bioactive molecules of interest can first be induced in prokaryotic cells to express desirable precursers (e.g. backbone molecules which will be capable of being modified) which can then be screened in another host system which allows the expression of active molecules. Particulary preferred prokaryotic cells are *E. coli* cells. Alternatively, crude or partially purified extracts, or pure proteins from metabolically rich cell lines can be combined with the original gene expression libraries to create potentially active molecules, which can then be screened for an activity of interest.

For example, gene libraries can be generated in *E.coli* as a host, and a shuttle vector as the vector, according to the examples provided herein. These libraries may then be screened using "hybridization screening". "Hybridization screening" is an approach used to detect pathways encoding compounds related to previously characterized small molecules which relies on the hybridization of probes to conserved genes within the pathway. This approach appears effective for the polyketide class of molecules which have highly conserved regions within the polyketide synthase genes in the pathway. Because of the highly conserved nature of these genes, hybridization of probes to high density filter arrays of clones from low complexity libraries is an effective approach to identify clones carrying potential full length pathways. Alternatively, multiplex PCR using primers designed against the conserved pathway genes can be used on DNA pools from clones arrayed in microtiter dish format.

Libraries made from complex communities require an enrichment procedure to increase the likelihood of identifying by hybridization any clones carrying homologous sequences. For example, the ~100 million base pairs of DNA immobilized on the filter shown in FIG. 3 represents approximately 5-fold coverage of 3 typical Streptomyces genomes. However, a gram of soil can contain approximately $10^6$ bacterial cells representing over $10^4$ species. Screening a library made from such a sample would require over 3,000 filters.

The biopanning approach described above can be used to create libraries enriched with clones carrying sequences homologous to a given probe sequence. Using this approach libraries containing clones with inserts of up to 40 kbp can be enriched approximately 1,000 fold after each round of panning. This enables one to reduce the above 3,000 filter fosmid library to 3 filters after 1 round of biopanning enrichment. This approach can be applied to create libraries enriched for clones carrying polyketide sequences.

Hybridization screening using high density filters or biopanning has proven an efficient approach to detect homologues of pathways containing conserved genes. To discover novel bioactive molecules that may have no known counterparts, however, other approaches are necessary. Another approach of the present invention is to screen in E. coli for the expression of small molecule ring structures or "backbones". Because the genes encoding these polycyclic structures can often be expressed in E. coli the small molecule backbone can be manufactured albeit in an inactive form. Bioactivity is conferred upon transferring the molecule or pathway to an appropriate host that expresses the requisite glycosylation and methylation genes that can modify or "decorate" the structure to its active form. Thus, inactive ring compounds, recombinantly expressed in E. coli are detected to identify clones which are then shuttled to a metabolically rich host, such as Streptomyces, for subsequent production of the bioactive molecule. The use of high throughput robotic systems allows the screening of hundreds of thousands of clones in multiplexed arrays in microtiter dishes.

One approach to detect and enrich for clones carrying these structures is to use FACS screening, a procedure described and exemplified in U.S. Ser. No. 08/876,276, filed Jun. 16, 1997. Polycyclic ring compounds typically have characteristic fluorescent spectra when excited by ultraviolet light. Thus clones expressing these structures can be distinguished from background using a sufficiently sensitive detection method. High throughput FACS screening can be utilized to screen for small molecule backbones in E. coli libraries. Commercially available FACS machines are capable of screening up to 100,000 clones per second for UV active molecules. These clones can be sorted for further FACS screening or the resident plasmids can be extracted and shuttled to Streptomyces for activity screening.

Figure 5:
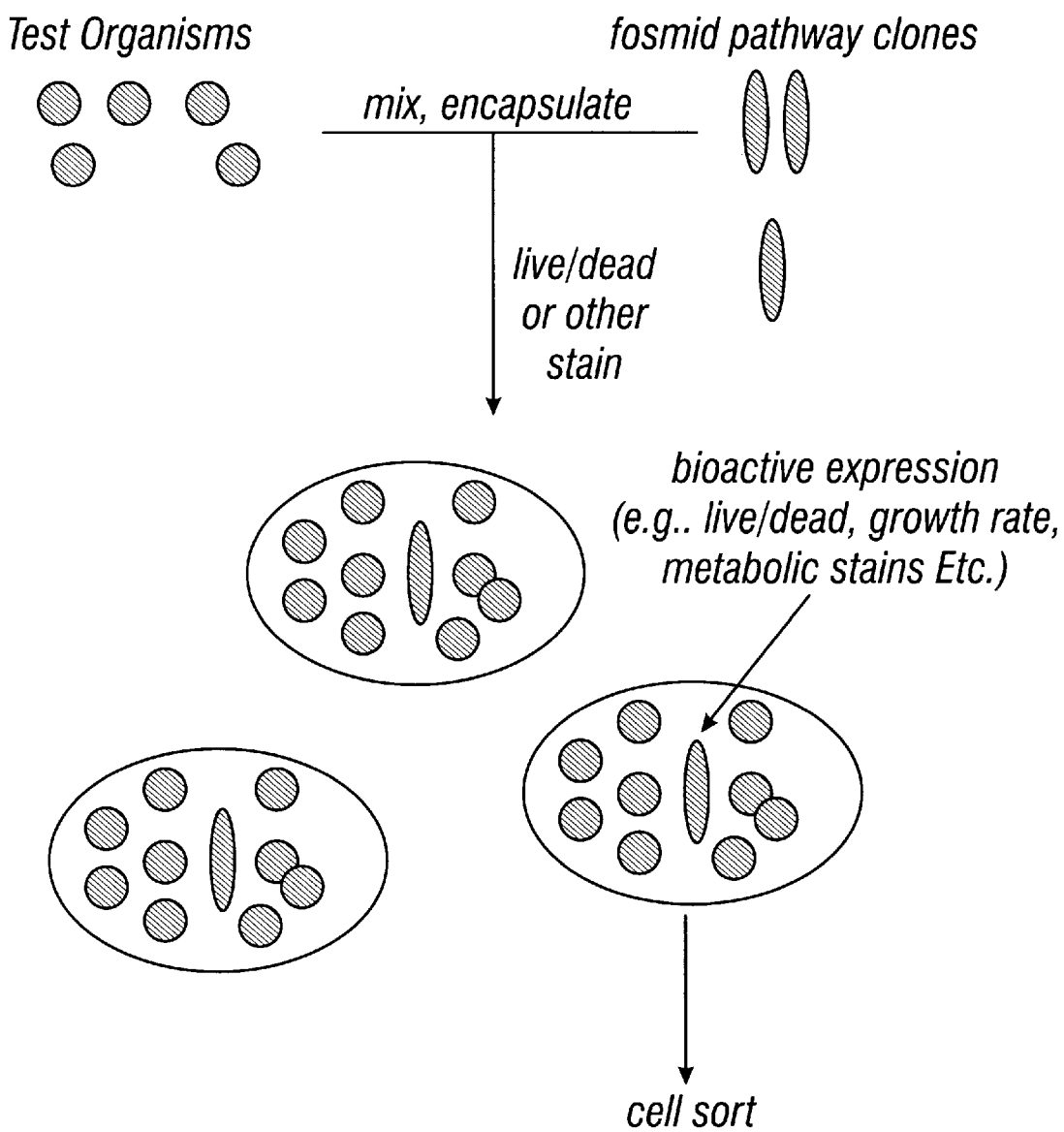
FIG. 5 shows a strategy for FACS screening for recombinant bioactive molecules in Streptomyces venezuelae.

In an alternate screening approach, after shuttling to Streptomyces hosts, organic extracts from candidate clones can be tested for bioactivity by susceptibility screening against test organisms such as *Staphylococcus aureus, E. coli,* or *Saccharomyces cervisiae*. FACS screening can be used in this approach by co-encapsulating clones with the test organism (FIG. 5).

An alternative to the abovementioned screening methods provided by the present invention is an approach termed "mixed extract" screening. The "mixed extract" screening approach takes advantage of the fact that the accessory genes needed to confer activity upon the polycyclic backbones are expressed in metabolically rich hosts, such as Streptomyces, and that the enzymes can be extracted and combined with the backbones extracted from E. coli clones to produce the bioactive compound in vitro. Enzyme extract preparations from metabolically rich hosts, such as Streptomyces strains, at various growth stages are combined with pools of organic extracts from E. coli libraries and then evaluated for bioactivity. A description of this is provided in the examples below.

Another approach to detect activity in the E. coli clones is to screen for genes that can convert bioactive compounds to different forms. For example, a recombinant enzyme was recently discovered that can convert the low value daunomycin to the higher value doxorubicin. Similar enzyme pathways are being sought to convert penicillins to cephalosporins.

Figure 6:
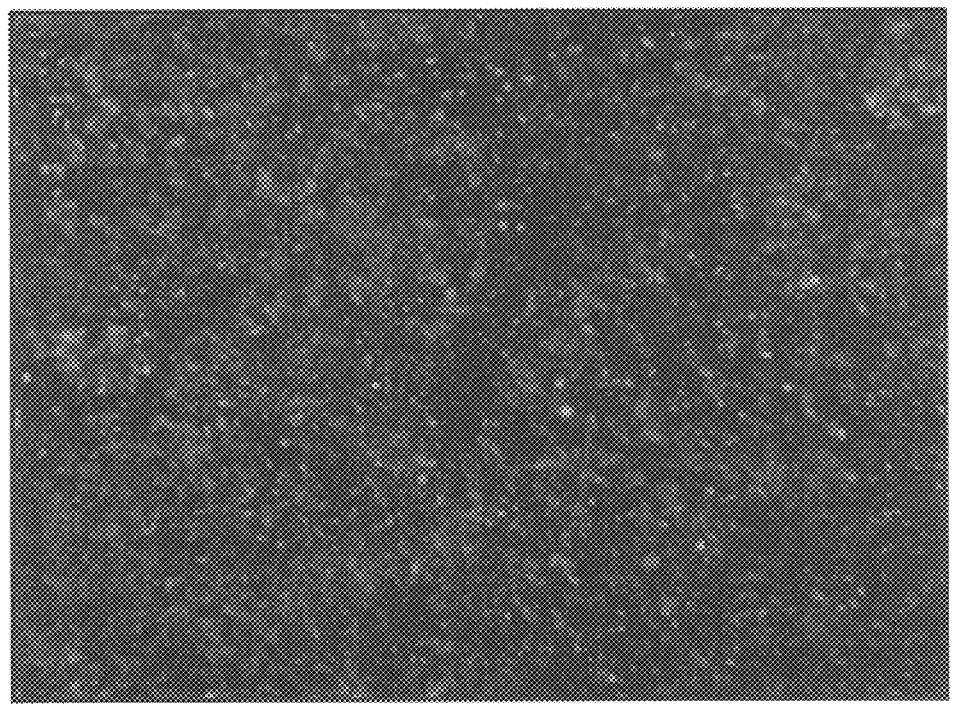
FIG. 6 shows a micrograph of pMF4 oxytetracyclin clone expressed in S. lividans strain TK24. The red fluorescence near the end of the mycelia suggests that recombinant expression of oxytetracyclin may be induced at the onset sporulation as is the activity of the endogenous actinorhodin pathway.

FACS screening can also be used to detect expression of UV fluorescent molecules in metabolically rich hosts, such as Streptomyces. Recombinant oxytetracylin retains its diagnostic red fluorescence when produced heterologously in *S. lividans* TK24 (FIG. 6). Pathway clones, which can be sorted by FACS, can thus be screened for polycyclic molecules in a high throughput fashion.

Figure 7:
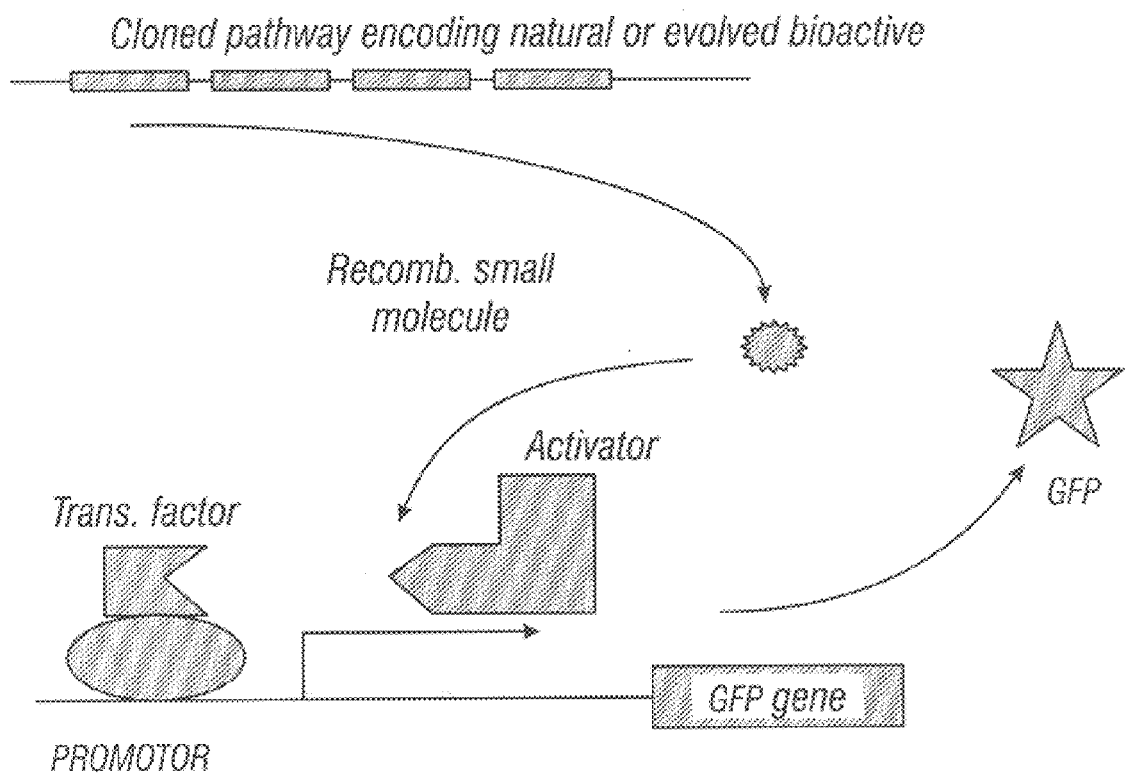
FIG. 7 shows an approach to screen for small molecules that enhance or inhibit transcription factor initiation. Both the small molecule pathway and the GFP reporter construct are co-expressed. Clones altered in GFP expression can then be sorted by FACS and the pathway clone isolated for characterization.

Recombinant bioactive compounds can also be screened in vivo using "two-hybrid" systems, which can detect enhancers and inhibitors of protein—protein or other interactions such as those between transcription factors and their activators, or receptors and their cognate targets. FIG. 7 depicts an approach to screen for small molecules that enhance or inhibit transcription factor initiation. Both the small molecule pathway and the GFP reporter construct are co-expressed. Clones altered in GFP expression can then be sorted by FACS and the pathway clone isolated for characterization.

As indicated, common approaches to drug discovery involve screening assays in which disease targets (macromolecules implicated in causing a disease) are exposed to potential drug candidates which are tested for therapeutic activity. In other approaches, whole cells or organisms that are representative of the causative agent of the disease, such as bacteria or tumor cell lines, are exposed to the potential candidates for screening purposes. Any of these approaches can be employed with the present invention.

The present invention also allows for the transfer of cloned pathways derived from uncultivated samples into metabolically rich hosts for heterologous expression and downstream screening for bioactive compounds of interest using a variety of screening approaches briefly described above.

Recovering Desirable Bioactivities

After viable or non-viable cells, each containing a different expression clone from the gene library are screened, and positive clones are recovered, DNA is isolated from positive clones utilizing techniques well known in the art. The DNA can then be amplified either in vivo or in vitro by utilizing any of the various amplification techniques known in the art. In vivo amplification would include transformation of the clone(s) or subclone(s) of the clones into a viable host, followed by growth of the host. In vitro amplification can be performed using techniques such as the polymerase chain reaction.

Evolution

One advantage afforded by a recombinant approach to the discovery of novel bioactive compounds is the ability to manipulate pathway subunits to generate and select for variants with altered specificity. Pathway subunits can be substituted or individual subunits can be evolved utilizing methods described below, to select for resultant bioactive molecules with different activities.

Clones found to have the bioactivity for which the screen was performed can be subjected to directed mutagenesis to develop new bioactivities with desired properties or to develop modified bioactivities with particularly desired properties that are absent or less pronounced in the wild-type activity, such as stability to heat or organic solvents. Any of the known techniques for directed mutagenesis are applicable to the invention. For example, particularly preferred mutagenesis techniques for use in accordance with the invention include those described below.

The term "error-prone PCR" refers to a process for performing PCR under conditions where the copying fidelity of the DNA polymerase is low, such that a high rate of point mutations is obtained along the entire length of the PCR product. Leung, D. W., et al., Technique, 1:11–15 (1989) and Caldwell, R. C. & Joyce G. F., PCR Methods Applic., 2:28–33 (1992).

The term "oligonucleotide directed mutagenesis" refers to a process which allows for the generation of site-specific mutations in any cloned DNA segment of interest. Reidhaar-Olson, J. F. & Sauer, R. T., et al., Science, 241:53–57 (1988).

The term "assembly PCR" refers to a process which involves the assembly of a PCR product from a mixture of small DNA fragments. A large number of different PCR reactions occur in parallel in the same vial, with the products of one reaction priming the products of another reaction.

The term "sexual PCR mutagenesis" (also known as "DNA shuffling") refers to forced homologous recombination between DNA molecules of different but highly related DNA sequence in vitro, caused by random fragmentation of the DNA molecule based on sequence homology, followed by fixation of the crossover by primer extension in a PCR reaction. Stemmer, W. P., PNAS, USA, 91:10747–10751 (1994).

The term "in vivo mutagenesis" refers to a process of generating random mutations in any cloned DNA of interest which involves the propagation of the DNA in a strain of *E. coli* that carries mutations in one or more of the DNA repair pathways. These "mutator" strains have a higher random mutation rate than that of a wild-type parent. Propagating the DNA in one of these strains will eventually generate random mutations within the DNA.

The term "cassette mutagenesis" refers to any process for replacing a small region of a double stranded DNA molecule with a synthetic oligonucleotide "cassette" that differs from the native sequence. The oligonucleotide often contains completely and/or partially randomized native sequence.

The term "recursive ensemble mutagenesis" refers to an algorithm for protein engineering (protein mutagenesis) developed to produce diverse populations of phenotypically related mutants whose members differ in amino acid sequence. This method uses a feedback mechanism to control successive rounds of combinatorial cassette mutagenesis. Arkin, A. P. and Youvan, D. C., PNAS, USA, 89:7811–7815 (1992).

The term "exponential ensemble mutagenesis" refers to a process for generating combinatorial libraries with a high percentage of unique and functional mutants, wherein small groups of residues are randomized in parallel to identify, at each altered position, amino acids which lead to functional proteins, Delegrave, S. and Youvan, D. C., Biotechnology Research, 11:1548–1552 (1993); and random and site-directed mutagenesis, Arnold, F. H., Current Opinion in Biotechnology, 4:450–455 (1993).

All of the references mentioned above are hereby incorporated by reference in their entirety. Each of these techniques is described in detail in the references mentioned. DNA can be mutagenized, or "evolved", utilizing any one or more of these techniques, and rescreened to identify more desirable clones. The invention will now be illustrated by the following working examples, which are in no way a limitation thereof.

EXAMPLE 1

Sample Collection Using a Microbial Containment Device

Sample to be utilized for downstream nucleic acid isolation for library generation may be collected according to the following example:

The following represents a method of selective in situ enrichment of bacterial and archaeal species while at the same time inhibiting the proliferation of eukaryotic members of the population.

In situ enrichment is achieved by using "traps" composed of growth substrates and nutritional amendments with the intent to lure, selectively, members of the surrounding environmental matrix, coated onto surfaces. Choice of substrates (carbon sources) and nutritional amendments (ie, nitrogen, phosphorous, etc.) is dependent upon the members of the community one desires to enrich. Selective agents against eukaryotic members are also added to the trap. Again, the exact composition will depend upon which members of the community one desires to enrich and which members of the community one desires to inhibit. Substrates include monomers and polymers. Monomers of substrates, such as glucosamine, cellulose, pentanoic or other acids, xylan, chitin, etc., can be utilized for attraction of certain types of microbes. Polymers can also be used to attract microbes that can degrade them. Some of the enrichment "media" which may be useful in pulling out particular members of the community is described below:

1. Addition of bioactive compounds against fungi and microscopic eukaryotes:

Proliferation of eukaryotic members of the community may be inhibited by the use of one or more commercially available compounds such as nystatin, cycloheximide, and/or pimaricin. These compounds may be sprinkled as a powder or incorporated as a liquid in the selective enrichment medium.

2. Addition of bioactive compounds against other bacterial species:

Compounds which inhibit the growth of some bacterial species but not others (ie, polymyxin, penicillin, and rifampin) may be incorporated into the enrichment medium. Use of the compounds is dependent upon which members of the bacterial community one desires to enrich. For example, while a majority of the Streptomyces are sensitive to polymyxin, penicillin, and rifampin, these may be used to enrich for "rare" members of the family which are resistant. Selective agents may also be used in enrichments for archaeal members of the community.

3. Use of carbon sources as selective agents:

Any particular carbon source can be utilized by some members of the community and not others. Carbon source selection thus depends upon the members of the community one desires to enrich. For example, members of the Streptomycetales tend to utilize complex, polymeric substrates such as cellulose, chitin, and lignin. These complex subtrates, while utilized by other genera, are recalcitrant to most bacteria. These complex substrates are utilized by fungi, which necessitates the use of anti-fungal agents, mentioned above.

4. Addition of nitrogen sources:

The use of additional nitrogen sources may be called for depending upon the choice for carbon source. For example, while chitin is balanced in its C:N ratio, cellulose is not. To enhance utilization of cellulose (or other carbon-rich substrates), it is often useful to add nitrogen soures such as nitrate or ammonia.

5. Addition of trace elements:

In general, the environmental matrix tends to be a good source of trace elements, but in certain environments, the elements may be limiting. Addition of trace elements may enhance growth of some members of the community while inhibiting others.

Large surface area materials, such as glass beads or silica aerogels can be utilized as surfaces in the present example. This allows a high concentration of microbes to be collected in a relatively small device holding multiple collections of substrate-surface conjugates.

Glass beads can be derivitized with N-Acetyl B-D-glucosamine-phenylisothiocyanate as follows:

Bead Preparation:

30 ml glass beads (Biospec Products, Bartlesville, Okla.) are mixed with 50 ml APS/Toluene (10% APS) (Sigma Chemical Co.)

Reflux overnight

Decant and wash 3 times with Toluene

Wash 3 times with ethanol and dry in oven

Derivitize with N-Acetyl B-D-glucosamine-phenylisothiocyanate as follows:

Combine in Falcon Tube:

25 ml prepared glass beads from above 15 ml 0.1M $NaHCO_3$+25 mg N-Acetyl-B-D-glucosamine-PITC (Sigma Chemical Co.)+1 ml DMSO Add 10 ml $NaHCO_3$+1 ml DMSO Pour over glass beads Let shake in Falcon Tube overnight Wash with 20 ml 0.1M $NaHCO_3$ Wash with 50 ml $ddH_2O$ Dry at 55° C. for 1 hour Beads can then be placed in mesh filter "bags" (Spectrum, Houston, Tex.) created to allow containment of the beads, while simultaneously allowing migration of microbes, which are then placed in any device used as a solid support which allows containment of the bag. Particularly preferred devices are made of inert materials, such as plexiglass. Alternatively, beads can be placed directly into Falcon Tubes (VWR, Fisher Scientific) which have been punctured with holes using a needle. These "containment" devices are then deployed in desired biotopes for a period of time to allow attraction and growth of desirable microbes. The following protocol details one method for generating a simple "microbial containment device":

Puncture holes using a heated needle or other pointed device into a 15 ml Falcon Tube (VWR, Fisher Scientific).

Place approximately 1–5 mls of the derivitized beads into a Spectra/mesh nylon filter, such as those available from Spectrum (Houston, Tex.) with a mesh opening of 70 m, an open area of 43%, and a thickness of 70 m. Seal the nylon filter to create a "bag" containing the beads using, for instance, Goop, Houshold Adhesive & Sealant.

Place the filter containing the beads into the ventilated Falcon Tube and deploy the tube into the desired biotope for a period of time (typically days).

EXAMPLE 2

DNA Isolation and Library Construction from Cultivated Organism

The following outlines the procedures used to generate a gene library from an isolate, *Streptomyces rimosus*.

Isolate DNA.

1. Inoculate 25 ml Trypticase Soy Broth (BBL Microbiology Systems) in 250 ml baffled erlenmeyer flasks with spores of *Streptomyces rimosus*. Incubate at 30° C. at 250 rpm for 48 hours.
2. Collect mycelin by centrifugation. Use 50 ml conical tubes and centrifuge at 25° C. at 4000 rpm for 10 minutes.
3. Decant supernatent and wash pellet 2× with 10 ml 10.3% sucrose (centrifuge as above between washes).
4. Store pellet at −20° C. for future use.
5. Resuspend pellet in 40 ml TE (10 mM Tris, 1 mM EDTA; pH 7.5) containing lysozyme (1 mg/ml; Sigma Chemical Co.)and incubate at 37° C. for 45 minutes.
6. Add sarcosyl (N-lauroylsarcosine, sodium salt, Sigma Chemical Co.) to final concentration of 1% and invert gently to mix for several minutes.
7. Transfer 20 ml of preparation to clean tube and add proteinase K (Stratagene Cloning Systems) to a final concentration of 1 mg/ml. Incubate overnight at 50° C.
8. Extract 2× with Phenol (saturated with TE).
9. Extract 1× with Phenol:$CH_3Cl$.
10. Extract 1× with $CH_3Cl$: Isoamyl alcohol.
11. Precipitate DNA with 2 volumes of EtOH.
12. Spool DNA on sealed pasteur pipet.
13. Rinse with 70% EtOH.
14. Dry in air.
15. Resuspend DNA in 1 ml TE and store at 4° C. to rehydrate slowly.
16. Check quality of DNA:

Digest 10 μl DNA with EcoRI restriction enzyme (Stratagene Cloning Systems) according to manufacturers protocol electrophorese DNA digest through 0.5% agarose, 20V overnight; stain gel in 1 g/ml EtBr
17. Determine DNA concentration ($A_{260}$–$A_{280}$).

Restriction Digest DNA

1. Incubate the following at 37° C. for 3 hours:

| | |
|---|---|
| 8 μl | DNA (~10 μg) |
| 35 μl | $H_2O$ |
| 5 μl | 10× restriction enzyme buffer |
| 2 μl | EcoRI restriction enzyme (200 units) |

Sucrose Gradient

1. Prepare small sucrose gradient (Sambrook, Fritsch and Maniatus, 1989) and run DNA at 45,000 rpm for 4 hours at 25° C.
2. Examine 5 μl of each fraction on 0.8% agarose gel.
3. Pool relevant fractions and precipitate DNA with 2.5 volumes of EtOH for 1 hour at −70° C.
4. Collect DNA by centrifugation at 13,200 rpm for 15 minutes.
5. Decant and wash with 1 ml of 70% EtOH.

6. Dry, resuspend in 15 μl TE.
7. Store at 4° C.

Dephosphorylate DNA
1. Dephosphorylate DNA with shrimp alkaline phosphatase according to manufacturers protocol (US Biochemicals).

Adaptor Ligation
1. Ligate adaptors according to manufacturers protocol.
2. Briefly, gently resuspend DNA in EcoR I-BamH I adaptors (Stratagene Cloning Systems); add 10× ligation buffer, 10 mM rATP, and T4 DNA ligase and incubate at room temperature for 4–6 hours.

Preparation of Fosmid Arms
1. Fosmid aims can be prepared as described (Kim, et.al., Nucl. Acids Res., 20:10832–10835, 1992). Plasmid DNA can be digested with PmeI restriction enzyme (New England Biolabs) according to the manufacturers protocol, dephosphorylated (Sambrook, Fritsch and Maniatus, 1989), followed by a digestion with BamH I restriction enzyme (New England Biolabs) according to the manufacturers protocol, and another dephosphorylation step to generate two arms each of which contain a cos site in the proper orientation for the cloning and packaging of ligated DNA between 35–45 kbp.

Ligation to Fosmid Arms
1. Prepare the ligation reaction:
   Add ~50 ng each of insert and vector DNA to 1 U of T4 DNA ligase (Boehringer Mannheim) and 10× ligase buffer as per manufacturers instructions; add $H_2O$ if necessary, to total of 10 μl.
2. Incubate overnight at 16° C.

Package and Plate
I. Package the ligation reactions using Gigapack XL packaging system (Stratagene Cloning Systems, Inc.) following manufacturer's protocol.
2 Transfect *E.coli* strain DH10B (Bethesda Research Laboratories, Inc.) according to manufacturers protocol and spread onto LB/Chloramphenicol plates (Sambrook, Fritsch and Maniatus, 1989).

EXAMPLE 3

Preparation of an Uncultivated Prokaryotic DNA Library

FIG. 1 shows an overview of the procedures used to construct an environmental library from a mixed picoplankton sample. The goal was to construct a stable, large insert DNA library representing picoplankton genomic DNA.

Cell collection and preparation of DNA. Agarose plugs containing concentrated picoplankton cells were prepared from samples collected on an oceanographic cruise from Newport, Oreg. to Honolulu, Hi. Seawater (30 liters) was collected in Niskin bottles, screened through 10 μm Nitex, and concentrated by hollow fiber filtration (Amicon DC10) through 30,000 MW cutoff polysulfone filters. The concentrated bacterioplankton cells were collected on a 0.22 μm, 47 mm Durapore filter, and resuspended in 1 ml of 2× STE buffer (1M NaCl, 0.1M EDTA, 10 mM Tris, pH 8.0) to a final density of approximately $1 \times 10^{10}$ cells per ml. The cell suspension was mixed with one volume of 1% molten Seaplaque LMP agarose (FMC) cooled to 40° C., and then immediately drawn into a 1 ml syringe. The syringe was sealed with parafilm and placed on ice for 10 min. The cell-containing agarose plug was extruded into 10 ml of Lysis Buffer (10 mM Tris pH 8.0, 50 mM NaCl, 0.1M EDTA, 1% Sarkosyl, 0.2% sodium deoxycholate, a mg/ml lysozyme) and incubated at 37° C. for one hour. The agarose plug was then transferred to 40 mls of ESP Buffer (1% Sarcosyl, 1 mg/ml proteinase-K, in 0.5M EDTA), and incubated at 55° C. for 16 hours. The solution was decanted and replaced with fresh ESP Buffer, and incubated at 55° C. for an additional hour. The agarose plugs were then placed in 50 mM EDTA and stored at 4° C. shipboard for the duration of the oceanographic cruise.

One slice of an agarose plug (72 μl) prepared from a sample collected off the Oregon coast was dialyzed overnight at 4° C. against 1 ml of buffer A (100 mM NaCl, 10 mM Bis Tris Propane-HCl, 100 g/ml acetylated BSA: pH 7.0 @ 25° C.) in a 2 ml microcentrifuge tube. The solution was replaced with 250 1 of fresh buffer A containing 10 mM $MgCl_2$ and 1 mM DTT and incubated on a rocking platform for 1 hr at room temperature. The solution was then changed to 250 μl of the same buffer containing 4 U of Sau3A1 (NEB), equilibrated to 37° C. in a water bath, and then incubated on a rocking platform in a 37° C. incubator for 45 min. The plug was transferred to a 1.5 ml microcentrifuge tube and incubated at 68° C. for 30 min to inactivate the protein, e.g. enzyme, and to melt the agarose. The agarose was digested and the DNA dephosphorylased using Gelase and HK-phosphatase (Epicentre), respectively, according to the manufacturer's recommendations. Protein was removed by gentle phenol/chloroform extraction and the DNA was ethanol precipitated, pelleted, and then washed with 70% ethanol. This partially digested DNA was resuspended in sterile $H_2O$ to a concentration of 2.5 ng/l for ligation to the pFOS1 vector.

PCR amplification results from several of the agarose plugs (data not shown) indicated the presence of significant amounts of archaeal DNA. Quantitative hybridization experiments using rRNA extracted from one sample, collected at 200 m of depth off the Oregon Coast, indicated that planktonic archaea in (this assemblage comprised approximately 4.7% of the total picoplankton biomass (this sample corresponds to "PACI"-200 m in Table 1 of DeLong et al., high abundance of Archaea in Antarctic marine picoplankton, *Nature*, 371:695–698, 1994). Results from archaeal-biased rDNA PCR amplification performed on agarose plug lysates confirmed the presence of relatively large amounts of archaeal DNA in this sample. Agarose plugs prepared from this picoplankton sample were chosen for subsequent fosmid library preparation. Each 1 ml agarose plug from this site contained approximately $7.5 \times 10^5$ cells, therefore approximately $5.4 \times 10^5$ cells were present in the 72 μl slice used in the preparation of the partially digested DNA.

Vector arms are prepared from pFOS1 as described (Kim et al., Stable propagation of cosmid sized human DNA inserts in an F factor based vector, Nucl. Acids Res., 20.10832–10835, 1992). Briefly, the plasmid is completely digested with AstII, dephosphorylated with HK phosphatase, and then digested with BamHI to generate two arms, each of which contains a cos site in the proper orientation for cloning and packaging ligated DNA between 35–45 kbp. The partially digested picoplankton DNA is ligated overnight to the pFOS1 arms in a 15 μl ligation reaction containing 25 ng each of vector and insert and 1 U of T4 DNA ligase (Boehringer-Mannheim). The ligated DNA in four microliters of this reaction is in vitro packaged using the Gigapack XL packaging system (Stratagene), the fosmid particles transfected to *E. coli* strain DH10B (BRL), and the cells spread onto $LB_{cm15}$ plates. The resultant fosmid clones are picked into 96-well microliter dishes containing $LB_{cm15}$ supplemented with 7% glycerol. Recombinant fosmids, each containing 40 kb of picoplankton DNA insert, have yielded a library of 3,552 fosmid clones, containing approximately 1.4×10⁸ base pairs of cloned DNA. All of the clones examined contained inserts ranging from 38 to 42 kbp. This library is stored frozen at −80° C. for later analysis.

EXAMPLE 4

Normalization of DNA from Environmental Samples

Prior to library generation, purified DNA from an environmental sample can be normalized. DNA is first fractionated according to the following protocol: Sample composed of genomic DNA is purified on a cesium-chloride gradient. The cesium chloride (Rf=1.3980) solution is filtered through a 0.2 Mm filter and 15 ml is loaded into a 35 ml OptiSeal tube (Beckman). The DNA is added and thoroughly mixed. Ten micrograms of bis-benzimide (Sigma; Hoechst 33258) is added and mixed thoroughly. The tube is then filled with the filtered cesium chloride solution and spun in a VTi50 rotor in a Beckman L8-70 Ultracentrifuge at 33,000 rpm for 72 hours. Following centrifugation, a syringe pump and fractionator (Brandel Model 186) are used to drive the gradient through an ISCO UA-5 UV absorbance detector set to 280 nm. Peaks representing the DNA from the organisms present in an environmental sample are obtained.

Normalization is then accomplished as follows:
1. Double-stranded DNA sample is resuspended in hybridization buffer (0.12 M NaH$_2$PO$_4$, pH 6.8/0.82 M NaCl/1 mM EDTA/0.1% SDS).
2. Sample is overlaid with mineral oil and denatured by boiling for 10 minutes.
3. Sample is incubated at 68° C. for 12–36 hours.
4. Double-stranded DNA is separated from single-stranded DNA according to standard protocols (Sambrook, 1989) on hydroxyapatite at 60° C.
5. The single-stranded DNA fraction is desalted and amplified by PCR.

The process is repeated for several more rounds (up to 5 or more).

EXAMPLE 5

Hybridization Screening of Libraries Generated in Prokaryotes and Expression Screening in Metabolically Rich Hosts Hybridization screening may be performed on fosmid clones from a library generated according to the protocol described in Example 3 above in any fosmid vector. For instance, the pMF3 vector is a fosmid based vector which can be used for efficient yet stable cloning in E. coli and which can be integrated and maintained stably in Streptomyces coelicolor or Streptomyces lividans. A pMF3 library generated according to the above protocol is first transformed into E. coli DH10B cells. Chloramphenicol resistant transformants containing tcm or oxy are identified by screening the library by colony hybridization using sequences designed from previously published sequences of oxy and tcm genes. }(27, }28) Colony hybridization screening is described in detail in "Molecular Cloning", A Laboratory Manual, Sambrook, et al., (1989) 1.90–1.104. Colonies that test positive by hybridization can be purified and their fosmid clones analyzed by restriction digestion and PCR to confirm that they contain the complete biosynthetic pathway Alternatively, DNA from the abovementioned fosmid clones may be used in a amplification reaction designed to identify clones positive for an entire pathway. For example, the following sequences may be employed in an amplification reaction to amplify a pathway encoding the antibiotic gramicidin (gramicidin operon), which resides on a 34 kbp DNA fragment potentially encoded on one fosmid clone:

Primers:

5'CACACGGATCCGAGCTCATCGATAGGCATGTGTTTAACTTCTTGTCATC3' SEQ ID NO:1

5'CTTATTGGATCCGAGCTCAATTGCTGAAGAGTTGAAGGAGAGCATCTTCC3' SEQ ID NO:2

Amplification reaction:

| | |
|---|---|
| 1 µl | fosmid/insert DNA |
| 5 µl | each primer (50 ng/µl) |
| 1 µl | Boehringer Mannheim EXPAND Polymerase from their EXPAND kit |
| 1 µl | dNTP's |
| 5 µl | 10X Buffer #3 from Boehringer Mannheim EXPAND kit |
| 30 µl | ddH$_2$O |

PCR Reaction Program:

| | |
|---|---|
| 94° C. | 60 seconds |
| 20 cycles of: | |
| 94° C. | 10 seconds |
| 65° C. | 30 seconds |
| 68° C. | 15 minutes |
| one cycle of: | |
| 68° C. | 7 minutes |
| Store at 4° C. | |

Fosmid DNA from clones that are shown to contain the oxytetracycline or tetracenomycin polyketide encoding DNA sequences are then used to transform S. lividans TK24 Dact protoplasts from Example 6. Transformants are selected by overlaying regeneration plates with hygromycin (pMF5). Resistant transformants are screened for bioactivity by overlaying transformation plates with 2 ml of nutrient soft agar containing cells of the test organisms Escherichia coli or Bacillus subtilis. E. coli is resistant to the thiostrepton concentration (50 mg/ml) to be used in the overlays of pMF3 clones but is sensitive to oxytetracylin at a concentration of 5 mg/ml }(29). The B. subtilis test strain is rendered resistant to thiostrepton prior to screening by transforming with a thiostrepton marker carried on pHT315 }(30). Bioactivity is demonstrated by inhibition of growth of the particular test strain around the S. lividans colonies. To confirm bioactivity, presumptive active clones are isolated and cultures extracted using a moderately polar solvent, methanol. Extractions are prepared by addition of methanol in a 1:1 ratio with the clone fermentation broth followed by overnight shaking at 4° C. Cell debris and media solids in the aqueous phase are then be separated by centrifugation. Recombinantly expressed compounds are recovered in the solvent phase and may be concentrated or diluted as necessary. Extracts of the clones are aliquoted onto 0.25-inch filter disks, the solvent allowed to evaporate, and then placed on the surface of an overlay containing the assay organisms. Following incubation at appropriate temperatures, the diameter of the clearing zones is measured and recorded. Diode array HPLC, using authentic oxytetracyclin and tetracenomycin as standards, can be used to confirm expression of these antibiotics from the recombinant clones.

Rescue of chromosmally integrated pathways

Sequence analysis of chromosomally integrated pathways identified by screening can be performed for confirmation of the bioactive molecule. One approach which can be taken to rescue fosmid DNA from *S. lividans* clones exhibiting bioactivity against the test organisms is based on the observation that plasmid vectors containing IS117, such as pMF3, are present as circular intermediates at a frequency of 1 per 10–30 chromosomes. The presumptive positive clones can be grown in 25 ml broth cultures and plasmid DNA isolated by standard alkaline lysis procedures. Plasmid DNA preps are then used to transform *E. coli* and transformants are selected for $Cm^r$ by plating onto LB containing chloramphenicol (15 mg/ml). Fosmid DNA from the *E. coli* $Cm^r$ transformants is isolated and analyzed by restriction digestion analysis, PCR, and DNA sequencing.

EXAMPLE 6

Host Strain Construction

The following example describes modifications that can be performed on the *Streptomyces lividans* strain to make it useful for screening bioactive clones originally identified in *E.coli* according to Example 5.

Figure 8:
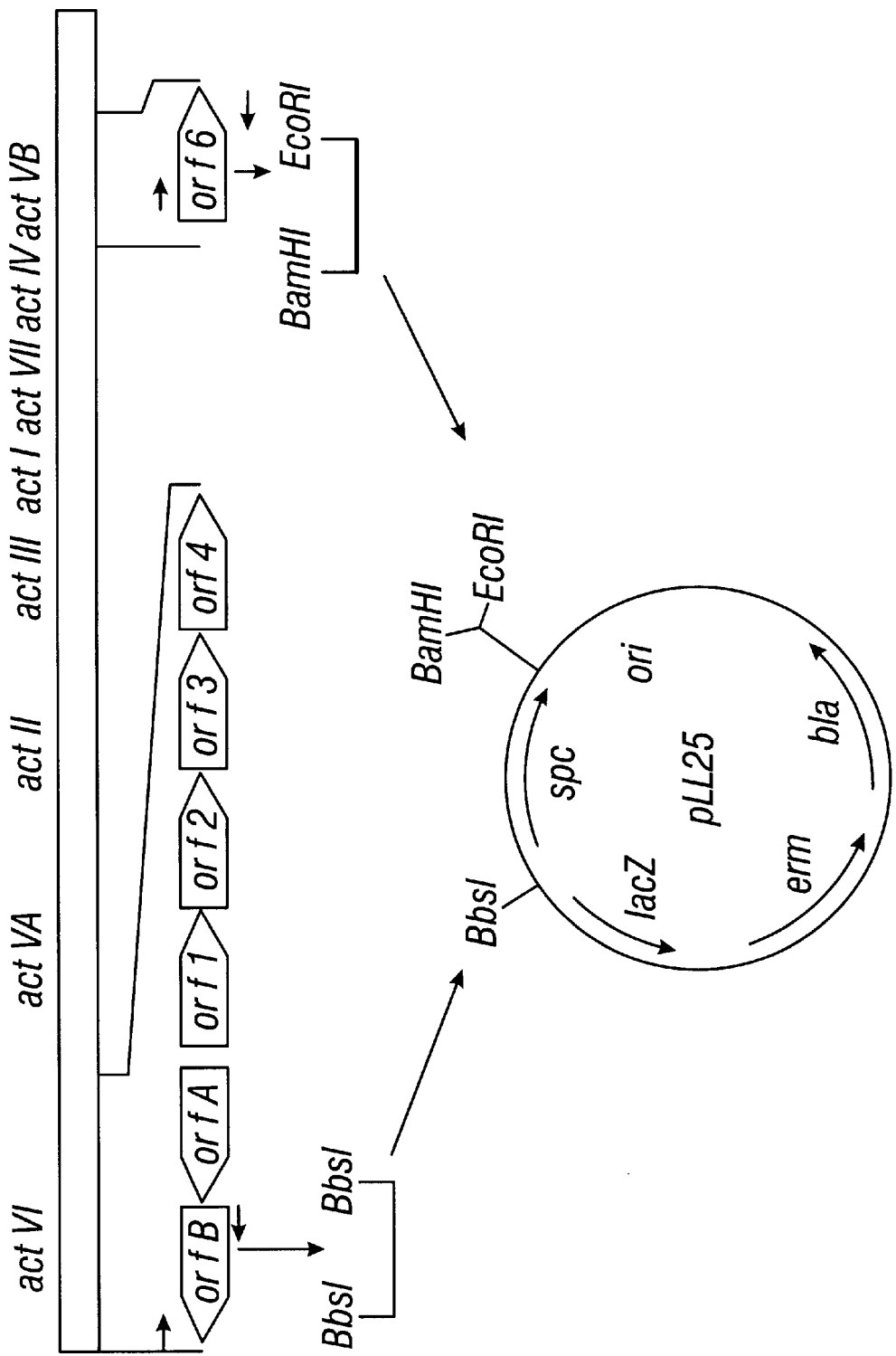
FIG. 8 shows the gene replacement vector pLL25 designed to inactivate the actinorhodin pathway in Streptomyces lividans strain TK24.
Figure 9:
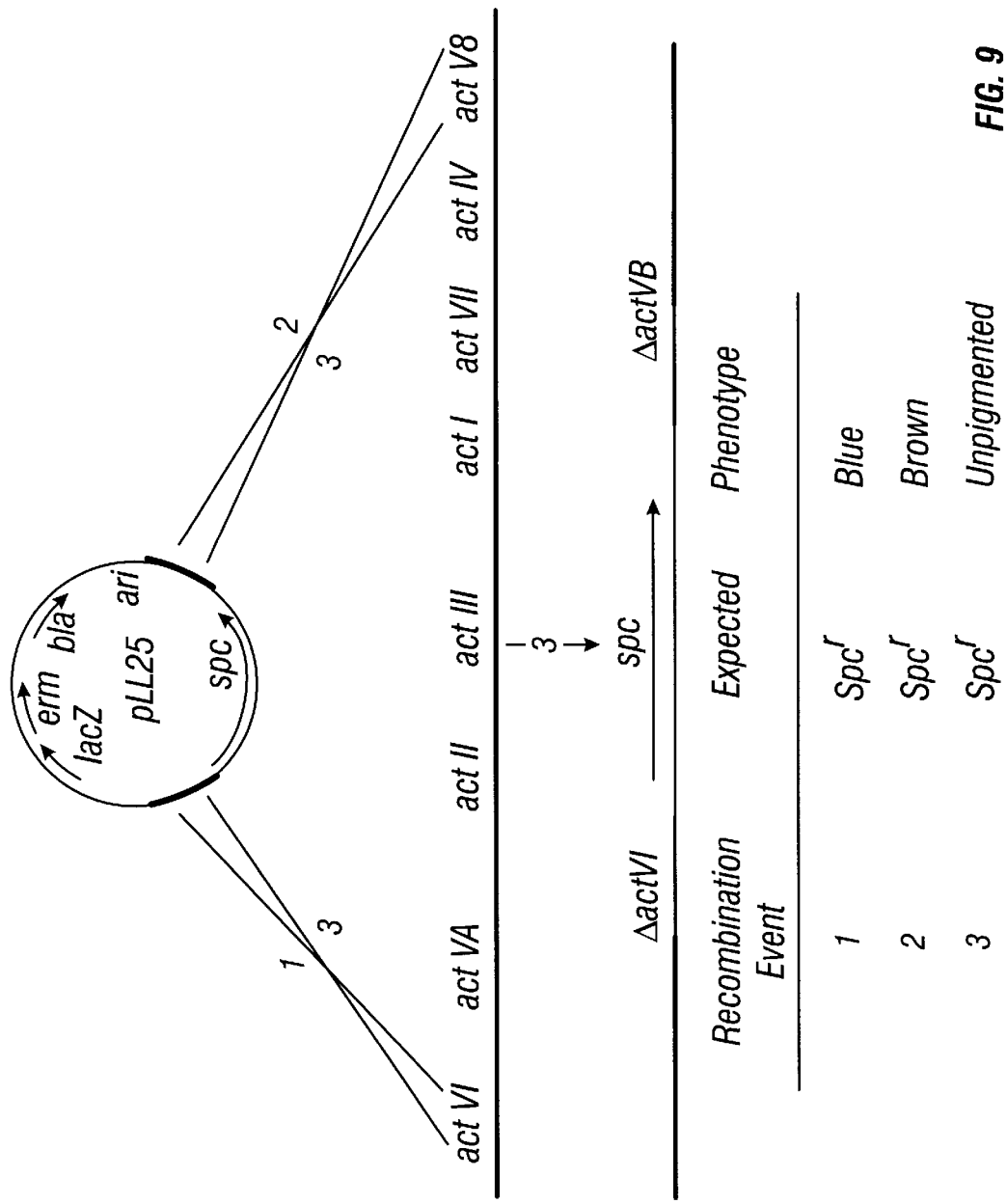
FIG. 9 shows the possible recombination events and predicted phenotypes from replacement of the actinorhodin gene cluster in S. lividans by the spectinomycin gene resident on pLL25.
Figure 10:
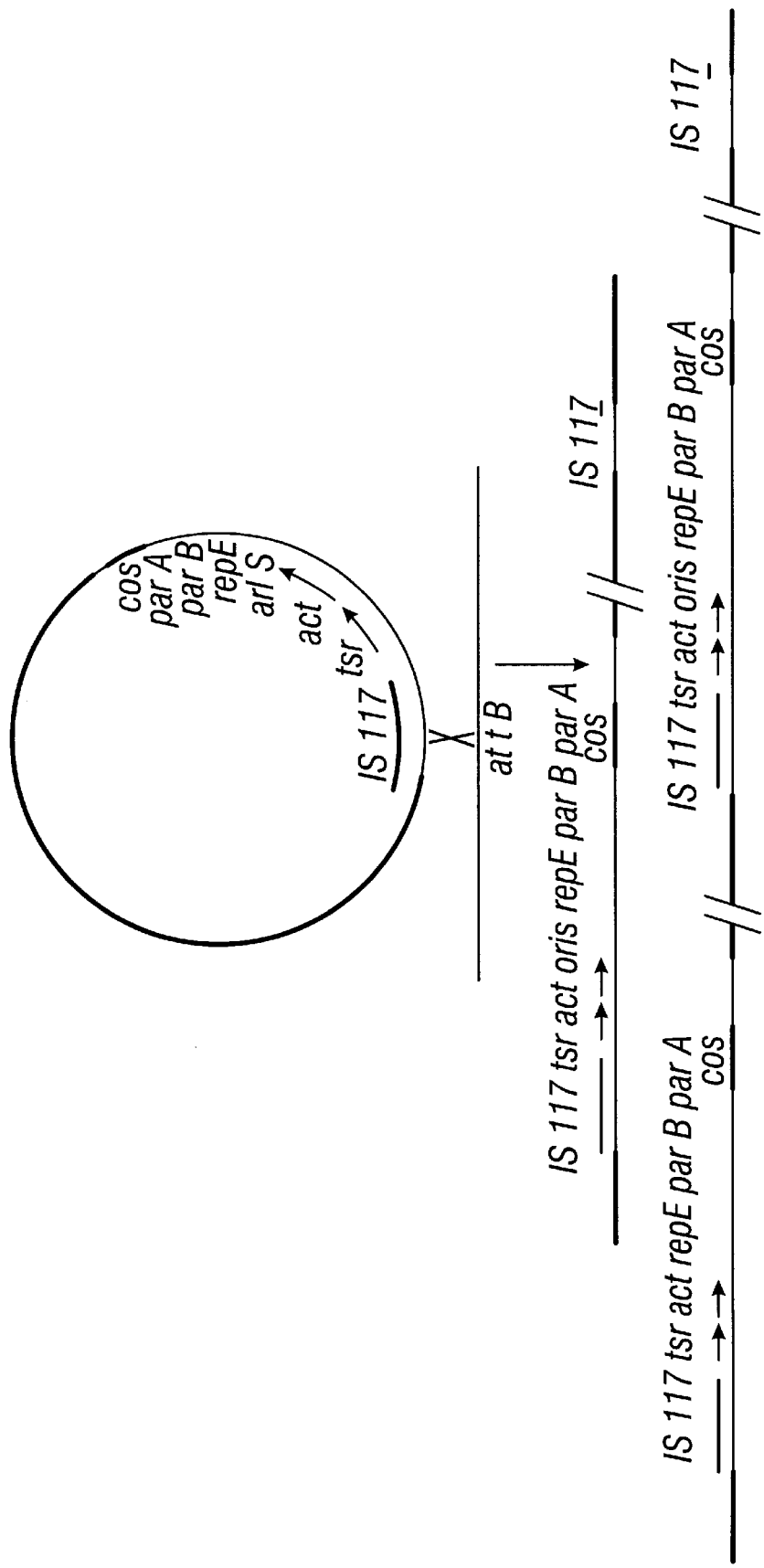
FIG. 10 shows a tandem duplication of a pMF3 clone into the S. lividans chromosome. Duplicated clones will contain cos sites at the appropriate spacing for lambda packaging.

*Streptomyces lividans* is a strain is routinely used in the recombinant expression of heterologous antibiotic pathways because it recognizes a large number of promoters and appears to lack a restriction system. Although *Streptomyces lividans* does not normally produce the polyketide antibiotic actinorhodin, it contains the requisite gene sequences, and several genes have been identified that activate its production in *S. lividans*. One strain of *S. lividans*, TK24, can be utilized as a host for screening for bioactive clones. This strain contains a mutation in the rpsL gene, encoding ribosomal protein S12, that confers resistance to streptomycin and activates the production of actinorhodin. In order to ensure that the bioactivity of *S. lividans* clones containing putative polyketide or other antibiotic genes is not due to the activation of the resident act gene cluster, these sequences should be removed from host strain by gene replacement. The outline for the gene replacement scheme is shown in FIG. 8. Gene fragments internal to actVI and actVB, which define the boundaries of the act cluster are amplified by PCR. The primers used for the amplification have recognition sequences designed within them so that they are cloned in the proper orientation respective to each other and the act cluster. The actVB and actVI gene fragments are cloned into pLL25 so that they flank the spectinomycin encoding gene, generating pRBSV2. *S. lividans* TK24 protoplasts are transformed with pRBSV2 using established transformation protocols and transformants are selected for spectinomycin resistance. As shown in FIG. 9, $Spc^r$ transformants can arise as a result of several recombination events. Single recombination events within actVI or actVB (events 1 and 2) result in the insertion of the plasmid construct within the act cluster. A double crossover within actVI and actVB (recombination event 3) results in the replacement of the act cluster with the $Spc^r$ encoding gene. While both types of recombinations can generate an $Act^-$ strain, the present example focuses on the construction of a strain containing the gene replacement. This is advantageous for two reasons: first, it generates a stable $Act^-$ strain that cannot revert to $Act^+$ by recombination between repeated sequences, and second, it decreases the amount of potential homology between cloned sequences and the chromosome, and decreases the likelihood of cloning partial pathways. Because the actinorhodin antibiotic is pigmented, one is able to distinguish the different classes of recombinants based on the pigment produced by the $Spc^r$ transformants. Only $Spc^r$ transformants that are generated by double recombination are non-pigmented. *S. lividans* TK24 clones that have the act cluster replaced by spc are confirmed by Southern hybridization and PCR analysis using standard techniques.

EXAMPLE 7

Screening of Large Insert Library for Compounds of Interest

Large insert libraries generated according to Examples 1 and 3 can be screened for potentially clinically valuable compounds of interest using the following method(s):

Organic Extraction of Fosmid Library Clones (aqueous):

Add equal volume of Methyl-Ethyl-Ketone (MEK)(Sigma Chemical Co.) to each well of the microtiter plate from Example 3. Transfer MEK phase to new plates. Spin plates to dry down. Resuspend sample(s) in TN Buffer (50 mM Tris-7, 10 mM NaCl).

Protein Extraction of Streptomycine

1. Inoculate 25 ml Trypticase Soy Broth (BBL Microbiology Systems) in 250 ml baffled erlenmeyer flasks with spores of *Streptomyces lividans* TK24. Incubate at 30° C. at 225 rpm for 48 hours.
2. Spin @ 4000 rpm in 50 ml conical to pellet cells (15 minutes).
3. Pour off supernatent and reserve.
4. Microscopically check pellet and supernatant.
5. Sonicate pellet
6. Pellet cell debris 4000 rpm/15 minutes (reserve).
7. Pull off supernatant.
8. Dialyze against 80% saturated Ammonium Sulfate solution according to manufacturers instructions (Slide-A-Lyzer™ Dialysis from Pierce.
9. Spin prep at 2500 rpm for 15 minutes.
10. Spin prep again at 3500 rpm for another 15 minutes.
11. Pull of supernatant and reserve.
12. Add 1 ml TN buffer (50 mM Tris pH 7; 100 mM NaCl)

In 1.5 ml screw caps, combine 50 1 aqueous extract from fosmid clones with 50 1 protein extract of Streptomycine (1:1 ratio) in assay wells.

Use different ratios of aqueous extract:protein extract (1:1 as indicated above, 3:1, etc.), as desired.

Incubate at 30° C. for 4 hours.

Bioassay

1. Spot 20 μl of sample onto filter disk.
2. Lay filter disk on previously generated assay plate (growth plate containing appropriate media to grow organism of interest, with an overlay of ~1 OD 600 of cells of test organism solidified into soft agar). Grow cells overnight at the appropriate incubation temperature for the test organism to grow. Identify clearing zones for positive results (inhibition of growth).

What is claimed is:

1. A method for identifying a desired activity encoded by a genomic DNA population comprising:

(a) obtaining a single-stranded genomic DNA population;

(b) contacting the single-stranded DNA population of (a) with a DNA probe bound to a ligand under conditions and for sufficient time to allow hybridization and to produce a double-stranded complex of probe and members of the genomic DNA population which hybridize thereto;

(c) contacting the double-stranded complex of (b) with a solid phase specific binding partner for said ligand so as to produce a solid phase complex;

(d) separating the solid phase complex from the single-stranded DNA population of (b);

(e) releasing from the probe the members of the genomic population which had bound to the solid phase bound probe;

(f) forming double-stranded DNA from the members of the genomic population of (e);

(g) introducing the double-stranded DNA of (f) into a suitable host cell to produce an expression library containing a plurality of clones containing and expressing the selected DNA;

(h) producing a cell-free extract of the expression library, (i) combining the expression library extract with a host cell-free protein extract from a metabolically rich host organism to form an extract mixture, and (j) screening the extract mixture for a desired activity resulting from the combining of the cell-free extracts.

2. The method of claim 1, wherein the genomic DNA population is derived from uncultivated or microorganisms.

3. The method of claim 2, wherein the uncultivated or cultivated microorganisms are isolated from an environmental sample.

4. The method of claim 3, wherein the microorganisms isolated from an environmental sample are extremophiles.

5. The method of claim 4, wherein the extremophiles are selected from the group consisting of thermophiles, hyperthermophiles, psychrophiles, halophiles, acidophiles, barophiles and psychrotrophs.

6. The method of claim 1, wherein the genomic DNA, or fragments thereof, comprise one or more operons, or portions thereof.

7. The method of claim 6, wherein the operons, or portions thereof, encodes a complete or partial metabolic pathway.

8. The method of claim 7, wherein the operons or portions thereof encoding a complete or partial metabolic pathway encodes polyketide syntheses.

9. The method of claim 1, wherein the expression library containing a plurality of clones is selected from the group consisting of phage, plasmids, phagemids, cosmids, phosmids, viral vectors and artificial chromosomes.

10. The method of claim 1, wherein the a suitable host cell is selected from the group consisting of a bacterium, fungus, plant cell, insect cell and animal cell.

11. The method of claim 1, wherein the DNA probe bound to a ligand is comprised of at least a portion of the coding region sequence of DNA for a known bioactivity.

12. The method of claim 1, wherein the ligand is selected from the group consisting of antigens or haptens, biotin or iminobiotin, sugars, enzymes, apoenzymes, homopolymeric oligonucleotides and hormones.

13. The method of claim 1, wherein the binding partner for said ligand is selected from the group consisting of antibodies or specific binding fragments thereof, avidin or streptavidin, lectins, enzyme inhibitors, apoenzyme cofactors, homopolymeric oligonucleotides and hormone receptors.

14. The method of claim 1, wherein a solid phase is selected from the group consisting of a glass or polymeric surface, a packed column of polymeric beads or magnetic or paramagnetic particles.

15. The method of claim 1, wherein the host organism is Streptomyces.

16. The method of claim 1, wherein the host organism is Bacillus.

17. A method for preselecting a desired DNA from a genomic DNA population comprising:

(a) obtaining a single-stranded genomic DNA population;

(b) contacting the single-stranded DNA population of (a) with a ligand-bound oligonucleotide probe that is complementary to a secretion signal sequence unique to a given class of proteins under conditions permissive of hybridization to form a double-stranded complex;

(c) contacting the double-stranded complex of (a) with a solid phase specific binding partner for said ligand so as to produce a solid phase complex;

(d) separating the solid phase complex from the single-stranded DNA population of (a);

(e) releasing the members of the genomic population which had bound to said solid phase bound probe;

(f) separating the solid phase bound probe from the members of the genomic population which hand bound thereto;

(g) forming double-stranded DNA from the members of the genomic population of (e);

(h) introducing the double-stranded DNA of (g) into a suitable host cell to form an expression library containing a plurality of clones containing the selected DNA;

(i) producing a cell-free extract of the expression library, (j) combining the expression library extract with a host cell-free protein extract from a metabolically rich host organism to form an extract mixture, and (k) screening the extract mixture for a desired activity resulting from the combining of the cell-free extracts.

18. The method of claim 17, wherein the genomic DNA population is derived from uncultivated or cultivated microorganisms.

19. The method of claim 17, wherein the uncultivated or cultivated microorganisms are isolated from an environmental sample.

20. The method of claim 19, wherein the microorganisms isolated from an environmental sample are extremophiles.

21. The method of claim 20, wherein the extremophiles are selected from the group consisting of thermophiles, hyperthermophiles, psychrophiles, halophiles, acidophiles, barophiles and psychrotrophs.

22. The method of claim 17, wherein the genomic DNA, or fragments thereof, comprise one or more operons, or portions thereof.

23. The method of claim 22, wherein the operons, or portions thereof, encodes a complete or partial metabolic pathway.

24. The method of claim 23, wherein the operons or portions thereof encoding a complete or partial metabolic pathway encodes polyketide synthases.

25. The method of claim 17, wherein the expression library containing a plurality of clones is selected from the group consisting of phage, plasmids, phagemids, cosmids, phosmids, viral vectors and artificial chromosomes.

26. The method of claim 17, wherein the a suitable host cell is selected from the group consisting of a bacterium, fungus, plant cell, insect cell and animal cell.

27. The method of claim 17, wherein the DNA probe bound to a ligand is comprised of at least a portion of the coding region sequence of DNA for a known bioactivity.

28. The method of claim 17, wherein the ligand is selected from the group consisting of antigens or haptens, biotin or iminobiotin, sugars, enzymes, apoenzymes, homopolymeric oligonucleotides and hormones.

29. The method of claim 17, wherein the binding partner for said ligand is selected from the group consisting of antibodies or specific binding fragments thereof, avidin or streptavidin, lectins, enzyme inhibitors, apoenzyme cofactors, homopolymeric oligonucleotides and hormone receptors.

30. The method of claim 17, wherein a solid phase is selected from the group consisting of a glass or polymeric surface, a packed column of polymeric beads or magnetic or paramagnetic particles.

31. The method of claim 17, wherein the host organism is Streptomyces.

32. The method of claim 17, wherein the host organism is Bacillus.

33. A method for identifying a desired bioactivity or biomolecule comprising:

(a) producing one or more expression libraries containing clones derived from nucleic acid directly isolated from the environment;

(b) producing a cell-free extract of proteins produced by the expression library, (c) combining the cell-free extract from expression library or libraries with crude or partially purified extracts, or pure proteins from a metabolically rich cell line to form an extract mixture free from the library and cell line cells, and (d) screening said mixture to identify an activity or molecule produced by the extract mixture.

* * * * *

UNITED STATES PATENT AND TRADEMARK OFFICE
CERTIFICATE OF CORRECTION

Page 1 of 1

PATENT NO.  : 6,057,103
DATED       : May 2, 2000
INVENTOR(S) : Jay M. Short

It is certified that error appears in the above-identified patent and that said Letters Patent is hereby corrected as shown below:

Please amend the claims in the issued patent as follows:

Column 31,
Line 64, claim 2, please delete "or microorganisms" and insert therefor --or cultivated microorganisms--.

Column 33,
Line 24, claim 17 (f), please delete "hand" and insert therefor --had--.
Line 42, claim 19, please delete "claim 17" and insert therefor --claim 18--.

Signed and Sealed this

Tenth Day of July, 2001

*Attest:*

*Attesting Officer*

NICHOLAS P. GODICI
*Acting Director of the United States Patent and Trademark Office*

SEQUENCE LISTING

<160> NUMBER OF SEQ ID NOS: 9

<210> SEQ ID NO 1
<211> LENGTH: 49
<212> TYPE: DNA
<213> ORGANISM: Artificial Sequence
<220> FEATURE:
<223> OTHER INFORMATION: Description of Artificial Sequence: pcr primer

<400> SEQUENCE: 1
cacacggatc cgagctcatc gataggcatg tgtttaactt cttgtcatc           49

<210> SEQ ID NO 2
<211> LENGTH: 50
<212> TYPE: DNA
<213> ORGANISM: Artificial Sequence
<220> FEATURE:
<223> OTHER INFORMATION: Description of Artificial Sequence: pcr primer

<400> SEQUENCE: 2
cttattggat ccgagctcaa ttgctgaaga gttgaaggag agcatcttcc          50

<210> SEQ ID NO 3
<211> LENGTH: 60
<212> TYPE: DNA
<213> ORGANISM: Artificial Sequence
<220> FEATURE:
<223> OTHER INFORMATION: Description of Artificial Sequence: pcr primer

<400> SEQUENCE: 3
gccgccgaca ccccgatcac gccgatcgtg gtgtcctgct tcgacgccat caaggcgacc    60

<210> SEQ ID NO 4
<211> LENGTH: 59
<212> TYPE: DNA
<213> ORGANISM: Artificial Sequence
<220> FEATURE:
<223> OTHER INFORMATION: Description of Artificial Sequence: pcr primer

<400> SEQUENCE: 4
gccgccgaca ccccgatcac cccgatcgtc gtcgcctgct tcgacgcgat ccgcgccac     59

<210> SEQ ID NO 5
<211> LENGTH: 60
<212> TYPE: DNA
<213> ORGANISM: Artificial Sequence
<220> FEATURE:
<223> OTHER INFORMATION: Description of Artificial Sequence: pcr primer

<400> SEQUENCE: 5
tcctcggacg ccccgatctc cccgatcacg atggcctgct tcgacgccat caaggcgacc    60

<210> SEQ ID NO 6
<211> LENGTH: 60
<212> TYPE: DNA
<213> ORGANISM: Artificial Sequence
<220> FEATURE:
<223> OTHER INFORMATION: Description of Artificial Sequence: pcr primer

<400> SEQUENCE: 6
gcggccgacg ccccgatctc gcccatcacc gtggcctgct tcgatgcgat caaggcgacc    60

<210> SEQ ID NO 7
<211> LENGTH: 59

```
<212> TYPE: DNA
<213> ORGANISM: Artificial Sequence
<220> FEATURE:
<223> OTHER INFORMATION: Description of Artificial Sequence: pcr primer

<400> SEQUENCE: 7
gccaccgacg cgccgatctc ccccatcacc gtggcctgct tcgacgccat caaggcgac      59

<210> SEQ ID NO 8
<211> LENGTH: 60
<212> TYPE: DNA
<213> ORGANISM: Artificial Sequence
<220> FEATURE:
<223> OTHER INFORMATION: Description of Artificial Sequence: pcr primer

<400> SEQUENCE: 8
gcggtggacg cgccgatcac cccgctcacg atggcggcct tcgacgcgat ccgcgccacc     60

<210> SEQ ID NO 9
<211> LENGTH: 60
<212> TYPE: DNA
<213> ORGANISM: Artificial Sequence
<220> FEATURE:
<223> OTHER INFORMATION: Description of Artificial Sequence: pcr primer

<400> SEQUENCE: 9
ggcgcagaga aagccagtac gccgctgggc gttggtggtt ttggcgcggc acgtgcatta    60
```